United States Patent
Chen et al.

(12)

(10) Patent No.: US 11,155,534 B2
(45) Date of Patent: *Oct. 26, 2021

(54) EGFR INHIBITOR FREE BASE OR ACID SALT POLYCRYSTALLINE FORM, PREPARATION METHOD THEREFOR, AND APPLICATION

(71) Applicants: JIANGSU HANSOH PHARMACEUTICAL GROUP CO., LTD., Jiangsu (CN); SHANGHAI HANSOH BIOMEDICAL CO., LTD., Shanghai (CN)

(72) Inventors: Zhongke Chen, Jiangsu (CN); Fuping Liu, Jiangsu (CN); Lei Liu, Jiangsu (CN); Rudi Bao, Jiangsu (CN)

(73) Assignees: Jiangsu Hansoh Pharmaceutical Group Co., Ltd., Jiangsu (CN); Shanghai Hansoh Biomedical Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/986,687

(22) Filed: Aug. 6, 2020

(65) Prior Publication Data

US 2020/0361909 A1    Nov. 19, 2020

Related U.S. Application Data

(63) Continuation of application No. 16/085,117, filed as application No. PCT/CN2016/111717 on Dec. 23, 2016, now Pat. No. 10,759,782.

(30) Foreign Application Priority Data

Mar. 22, 2016 (CN) .......................... 201610165018.6

(51) Int. Cl.
   *C07D 403/04* (2006.01)
   *A61P 35/00* (2006.01)
(52) U.S. Cl.
   CPC ............ *C07D 403/04* (2013.01); *A61P 35/00* (2018.01); *C07B 2200/13* (2013.01)
(58) Field of Classification Search
   None
   See application file for complete search history.

(56) References Cited

U.S. PATENT DOCUMENTS

| 3,609,152 | A | * | 9/1971 | Hess | .................... C07D 491/04 |
| | | | | | 540/600 |
| 4,337,341 | A | * | 6/1982 | Zimmerman | ........... C07C 45/68 |
| | | | | | 546/112 |
| 8,946,235 | B2 | | 2/2015 | Butterworth | |
| 10,759,782 | B2 | * | 9/2020 | Chen | ....................... A61P 35/00 |
| 2017/0008889 | A1 | | 1/2017 | Lan | |
| 2017/0313714 | A1 | | 11/2017 | Wei | |

FOREIGN PATENT DOCUMENTS

| CN | 103702990 A | 4/2014 |
| CN | 104860941 A | 8/2015 |
| WO | 2015195228 A1 | 12/2015 |
| WO | 2016/054987 A1 | 4/2016 |

OTHER PUBLICATIONS

Berge et al. J. of Pharmaceutical Sciences, vol. 66 p. 1-19 . (Year: 1977).*
Brittain et al, "Polymorphism in Pharmaceutical Solids," vol. 192, 2nd Ed. (2009).
Byrn et al, "Solid-State Chemistry to Drugs," 2nd Ed. (1999).
Mullin et al, "Programmed cooling of batch crystallizers," Chemical Engineering Science, vol. 26, pp. 369-377 (1971).
International Search Report dated Mar. 28, 2017 in International Application No. PCT/CN2016/111717.
International Preliminary Report on Patentability dated Sep. 25, 2018 in International Application No. PCT/CN2016/111717.

* cited by examiner

*Primary Examiner* — Emily A Bernhardt
(74) *Attorney, Agent, or Firm* — Ice Miller LLP

(57) ABSTRACT

Disclosed are an EGFR inhibitor free base or acid salt polycrystalline form, a preparation method therefor, and an application thereof. The present invention specifically relates to an N-(5-((4-(1-cyclopropyl-1H-indol-3-yl)pyrimidin-2-yl)amino)-2-((2-(dimethylamino)ethyl)(methyl) amino)-4-methoxyphenyl)acrylamide free base or acid salt polycrystalline form, a preparation method therefor, and an application of the polycrystalline form in preparing a drug for treating an EGFR mutant activity-mediated disease. The present invention is used for inhibiting the activity of an L858R EGFR mutant, a T790M EGFR mutant and an exon 19 deletion activating mutant etc., may be widely applied in preventing and treating cancer, especially non-small cell lung cancer and other related diseases, and is expected to develop into a new generation of EGFR inhibitors.

10 Claims, 11 Drawing Sheets

EGFR INHIBITOR FREE BASE OR ACID SALT POLYCRYSTALLINE FORM, PREPARATION METHOD THEREFOR, AND APPLICATION

CROSS-REFERENCE TO RELATED APPLICATIONS

This application is a continuation of U.S. patent application Ser. No. 16/085,117 filed Sep. 14, 2018, allowed Apr. 29, 2020, which is a Section 371 of International Application No. PCT/CN2016/111717, filed Dec. 23, 2016, which was published in the Chinese language on Sep. 28, 2017, under International Publication No. WO 2017/161937 A1, which claims priority under 35 U.S.C. § 119(b) to Chinese Application No. 201610165018.6, filed Mar. 22, 2016, the disclosures of which are incorporated herein by reference in their entirety.

FIELD OF THE INVENTION

The present invention belongs to the technical field of drug development, and specifically relates to a free base or acid salt polymorph of an EGFR inhibitor, a preparation method, and application thereof.

BACKGROUND OF THE INVENTION

EGFR (epidermal growth factor receptor) is a member of the erbB receptor family, which includes transmembrane protein tyrosine kinase receptors. By binding to its ligand, such as epidermal growth factor (EGF), EGFR can form a homodimer on the cell membrane or form a heterodimer with other receptors in the family, such as erbB2, erbB3, or erbB4. The formation of these dimers can cause the phosphorylation of key tyrosine residues in EGFR cells, thereby activating a number of downstream signaling pathways in cells. These intracellular signaling pathways play an important role in cell proliferation, survival and anti-apoptosis. Disorders of EGFR signal transduction pathways, including increased expression of ligands or receptors, EGFR gene amplification and mutation and the like, can promote malignant transformation of cells, and play an important role in tumor cell proliferation, or invasion, metastasis and angiogenesis. Therefore, EGFR is a reasonable target for the development of anticancer drugs.

Therefore, Jiangsu Hansoh Pharmaceutical Group Co., Ltd. developed a small molecule EGFR inhibitor in the patent application PCT/CN2015/091189 (a compound of formula I, the chemical name is: N-(5-((4-(1-cyclopropyl-1H-indol-3-yl)pyrimidin-2-yl)amino)-2-((2-(dimethylamino)ethyl)(methyl)amino)-4-methoxyphenyl)acrylamide), which has the following structure:

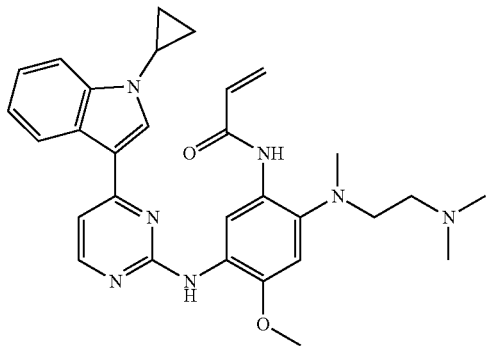

(I)

This small molecule EGFR inhibitor has high selectivity for inhibiting the EGFR T790M mutant, and has no or low activity to wild-type EGFR. Due to this high selectivity, the skin and gastrointestinal damage caused by inhibition of wild-type EGFR can be greatly reduced, and the drug-resistant tumor caused by the secondary mutation of EGFR-T790M can be treated. In addition, it makes sense to maintain the inhibitory activity to EGFR-activated mutant (including EGFR-L858R and delE746_A750 with exon 19 deletion). Due to the higher selectivity and safety of this small molecule EGFR inhibitor, it is expected to be developed into a clinical first-line therapeutic drug.

DESCRIPTION OF THE INVENTION

In order to solve the technical problems in the prior art, the inventors have intensively studied the different aggregation states of the free base or acid salt of the compound of formula I to obtain a number of the free base or acid salt polymorphs of the compound of formula I, which can greatly improve the physical and chemical properties of the amorphous form of the compound of formula I, such as crystallinity, solubility, hygroscopicity and chemical stability, and the process operability is improved, thereby screening out pharmaceutically acceptable, the most suitable aggregation state, and providing scientific basis for drug development.

In the first aspect, the present invention provides a free base or acid salt polymorph of the compound of formula I, i.e., N-(5-((4-(1-cyclopropyl-1H-indol-3-yl)pyrimidin-2-yl)amino)-2-((2-(dimethylamino)ethyl)(methyl)amino)-4-methoxyphenyl)acrylamide.

In a preferred embodiment, the acid salt comprises an inorganic acid salt or an organic acid salt.

In a further preferred embodiment, the inorganic acid salt is selected from the group consisting of hydrochloride, sulfate, hydrobromide, hydrofluoride, hydroiode and phosphate; preferably, the inorganic acid salt is selected from the group consisting of hydrochloride, sulfate and phosphate.

In a further preferred embodiment, the organic acid salt is selected from the group consisting of acetate, propionate, hexanoate, caprylate, fumarate, maleate, malonate, succinate, glutarate, adipate, sebacate, dichloroacetate, trichloroacetate, acetohydroxamate, salicylate, 4-aminosalicylate, benzoate, 4-acetylaminobenzoate, 4-aminobenzoate, caprate, cinnamate, citrate, aspartate, camphorate, gluconate, glucuronate, glutamate, erythorbate, lactate, aspartate, malate, mandelate, pyroglutamate, tartrate, lauryl sulfate, dibenzoyltartrate, 2,5-dihydroxybenzoate, 1-hydroxy-2-naphthoate, mesylate, ethyl-1,2-disulfonate, ethanesulfonate, benzenesulfonate, 4-chlorobenzenesulfonate, p-toluenesulfonate, cyclohexylsulfamate, camphorsulfonate, 1,5-naphthalenedisulfonate, naphthalene-2-sulfonate, formate, galactonate, gentisate, 2-ketoglutarate, glycolate, hippurate, isethionate, lactobionate, ascorbate, aspartate, laurate, camphorate, nicotinate, oleate, orotate, oxalate, palmitate, pamoate, stearate, thiocyanate, undecylenate, trifluoroacetate and succinate, preferably, the organic acid salt is selected from the group consisting of mesylate, fumarate, maleate and acetate.

In a still further preferred embodiment, the present invention provides a free base polymorph of the compound of formula I. The free base polymorph comprises three crystal forms, referred to as crystal form I, crystal form II and crystal form III of the free base, respectively.

The present invention provides a crystal form I of the free base of the compound of formula I having an X-ray powder diffraction spectrum comprising peaks at diffraction angles (2θ) of 24.4±0.2°, 15.1±0.2°, 25.2±0.2° and 7.4±0.2°.

Preferably, the X-ray powder diffraction spectrum further comprises peaks at diffraction angles (2θ) of 23.1±0.2°, 19.6±0.2°, 14.1±0.2°, 16.7±0.2° and 11.4±0.2°.

More preferably, the X-ray powder diffraction spectrum further comprises peaks at diffraction angles (2θ) of 24.9±0.2°, 20.6±0.2°, 22.7±0.2°, 9.7±0.2°, 26.1±0.2° and 21.8±0.2°.

Most preferably, the X-ray powder diffraction spectrum of crystal form I of the free base of the compound of formula I according to the present invention comprises substantially the same peaks at diffraction angles (2θ) as shown in FIG. 1, and the X-ray powder diffraction data are shown in Table 1:

TABLE 1

| 2θ (°) | intensity % |
|---|---|
| 7.4 | 55.2 |
| 9.7 | 15.8 |
| 10.8 | 11.2 |
| 11.4 | 28.8 |
| 14.1 | 38.4 |
| 15.1 | 65.5 |
| 15.5 | 9.0 |
| 16.7 | 37.2 |
| 17.8 | 7.5 |
| 18.5 | 10.3 |
| 19.6 | 39.9 |
| 20.6 | 23.9 |
| 21.8 | 11.5 |
| 22.7 | 16.8 |
| 23.1 | 44.2 |
| 24.4 | 100.0 |
| 24.9 | 25.6 |
| 25.2 | 58.3 |
| 26.1 | 14.7 |
| 30.4 | 10.9 |

The present invention provides a crystal form II of the free base of the compound of formula I having an X-ray powder diffraction spectrum comprising peaks at diffraction angles (2θ) of 18.9±0.2°, 25.9±0.2°, 31.6±0.2° and 21.0±0.2°.

Preferably, the X-ray powder diffraction spectrum further comprises peaks at diffraction angles (2θ) of 15.0±0.2°, 16.1±0.2°, 24.4±0.2°, 19.1±0.2° and 8.7±0.2°.

More preferably, the X-ray powder diffraction spectrum further comprises peaks at diffraction angles (2θ) of 8.4±0.2°, 10.4±0.2°, 22.0±0.2°, 17.7±0.2°, 22.5±0.2° and 26.4±0.2°.

Most preferably, the X-ray powder diffraction spectrum of crystal form II of the free base of the compound of formula I according to the present invention comprises substantially the same peaks at diffraction angles (2θ) as shown in FIG. 2, and the X-ray powder diffraction data are shown in Table 2:

TABLE 2

| 2θ (°) | intensity % |
|---|---|
| 8.4 | 41.4 |
| 8.7 | 47.3 |
| 9.5 | 19.6 |
| 10.4 | 40.1 |
| 15.0 | 58.7 |
| 16.1 | 57.6 |
| 17.7 | 37.9 |
| 18.6 | 21.4 |
| 18.9 | 100.0 |

TABLE 2-continued

| 2θ (°) | intensity % |
|---|---|
| 19.1 | 47.6 |
| 20.2° | 25.0 |
| 21.0 | 85.5 |
| 22.0 | 39.8 |
| 22.5 | 37.5 |
| 23.5 | 21.7 |
| 24.4 | 54.7 |
| 25.5 | 20.1 |
| 25.9 | 95.9 |
| 26.4 | 28.8 |
| 31.6 | 94.3 |

The present invention provides a crystal form III of the free base of the compound of formula I having an X-ray powder diffraction spectrum comprising peaks at diffraction angles (2θ) of 8.0±0.2°, 23.7±0.2°, 19.0±0.2° and 18.6±0.2°.

Preferably, the X-ray powder diffraction spectrum further comprises peaks at diffraction angles (2θ) of 23.9±0.2°, 16.1±0.2°, 22.5±0.2°, 22.1±0.2° and 11.1±0.2°.

More preferably, the X-ray powder diffraction spectrum further comprises peaks at diffraction angles (2θ) of 10.4±0.2°, 14.1±0.2°, 15.7±0.2°, 12.1±0.2°, 8.7±0.2° and 28.9±0.2°.

Most preferably, the X-ray powder diffraction spectrum of crystal form III of the free base of the compound of formula I according to the present invention comprises substantially the same peaks at diffraction angles (2θ) as shown in FIG. 3, and the X-ray powder diffraction data are shown in Table 3:

TABLE 3

| 2θ (°) | intensity % |
|---|---|
| 8.0 | 100.0 |
| 23.7 | 64.7 |
| 19.0 | 42.9 |
| 18.6 | 37.4 |
| 23.9 | 36.4 |
| 16.1 | 28.8 |
| 22.5 | 18.8 |
| 22.1 | 16.0 |
| 11.1 | 14.7 |
| 10.4 | 13.7 |
| 14.1 | 13.3 |
| 15.7 | 13.1 |
| 12.1 | 10.8 |
| 8.7 | 9.3 |
| 28.9 | 8.6 |
| 18.0 | 6.9 |
| 28.4 | 6.2 |
| 14.7 | 5.4 |
| 16.9 | 5.3 |
| 26.5 | 4.5 |

In a still further preferred embodiment, the present invention provides a crystal form I of a hydrochloride salt of the compound of formula I having an X-ray powder diffraction spectrum comprising peaks at diffraction angles (2θ) of 24.0±0.2°, 6.6±0.2°, 8.8±0.2° and 25.8±0.2°.

Preferably, the X-ray powder diffraction spectrum further comprises peaks at diffraction angles (2θ) of 14.2±0.2°, 21.6±0.2°, 6.9±0.2°, 25.2±0.2° and 27.0±0.2°.

More preferably, the X-ray powder diffraction spectrum further comprises peaks at diffraction angles (2θ) of 22.7±0.2°, 12.7±0.2°, 6.4±0.2°, 20.2±0.2°, 17.8±0.2° and 11.0±0.2°.

Most preferably, the X-ray powder diffraction spectrum of crystal form I of the hydrochloride salt of the compound of formula I according to the present invention comprises substantially the same peaks at diffraction angles (2θ) as shown in FIG. 4, and the X-ray powder diffraction data are shown in Table 4:

TABLE 4

| 2θ (°) | intensity % |
|---|---|
| 6.4 | 36.5 |
| 6.6 | 75.6 |
| 6.9 | 47.0 |
| 8.8 | 74.4 |
| 11.0 | 31.7 |
| 12.3 | 27.2 |
| 12.7 | 36.7 |
| 13.3 | 27.6 |
| 14.2 | 53.9 |
| 17.8 | 31.9 |
| 18.0 | 31.0 |
| 20.2 | 32.5 |
| 21.6 | 51.9 |
| 22.7 | 37.4 |
| 24.0 | 100.0 |
| 25.2 | 39.7 |
| 25.8 | 68.7 |
| 26.8 | 24.2 |
| 27.0 | 39.0 |
| 28.2 | 25.0 |

In a still further preferred embodiment, the present invention provides a sulfate salt polymorph of the compound of formula I in polycrystalline form. The sulfate salt polymorph comprises four crystal forms, referred to as crystal form I, crystal form II, crystal form III and crystal form IV, respectively.

The present invention provides a crystal form I of the sulfate salt of the compound of formula I having an X-ray powder diffraction spectrum comprising peaks at diffraction angles (2θ) of 16.3±0.2°, 11.9±0.2°, 13.7±0.2° and 22.3±0.2°.

Preferably, the X-ray powder diffraction spectrum further comprises peaks at diffraction angles (2θ) of 24.3±0.2°, 19.6±0.2°, 24.9±0.2°, 20.7±0.2° and 18.8±0.2°.

More preferably, the X-ray powder diffraction spectrum further comprises peaks at diffraction angles (2θ) of 24.0±0.2°, 8.5±0.2°, 10.5±0.2°, 17.8±0.2°, 21.9±0.2° and 22.8±0.2°.

Most preferably, the X-ray powder diffraction spectrum of crystal form I of the sulfate salt of the compound of formula I according to the present invention comprises substantially the same peaks at diffraction angles (2θ) as shown in FIG. 5, and the X-ray powder diffraction data are shown in Table 5:

TABLE 5

| 2θ (°) | intensity % |
|---|---|
| 8.5 | 44.3 |
| 8.8 | 26.7 |
| 10.5 | 44.1 |
| 11.9 | 90.9 |
| 13.7 | 76.6 |
| 15.6 | 31.4 |
| 16.3 | 100.0 |
| 17.2 | 30.4 |
| 17.8 | 43.4 |
| 18.8 | 51.0 |
| 19.6 | 57.6 |
| 20.7 | 51.6 |
| 21.9 | 42.5 |
| 22.3 | 74.2 |

TABLE 5-continued

| 2θ (°) | intensity % |
|---|---|
| 22.8 | 36.1 |
| 24.0 | 49.6 |
| 24.3 | 72.4 |
| 24.9 | 53.1 |
| 25.6 | 32.9 |
| 29.4 | 29.1 |

The present invention provides a crystal form II of the sulfate salt of the compound of formula I having an X-ray powder diffraction spectrum comprising peaks at diffraction angles (2θ) of 10.7±0.2°, 22.5±0.2°, 25.8±0.2° and 9.3±0.2°.

Preferably, the X-ray powder diffraction spectrum further comprises peaks at diffraction angles (2θ) of 21.6±0.2°, 15.8±0.2°, 19.9±0.2°, 18.9±0.2° and 22.2±0.2.

More preferably, the X-ray powder diffraction spectrum further comprises peaks at diffraction angles (2θ) of 14.0±0.2°, 27.9±0.2°, 11.5±0.2°, 23.0±0.2°, 31.7±0.2° and 24.0±0.2°.

Most preferably, the X-ray powder diffraction spectrum of crystal form II of the sulfate salt of the compound of formula I according to the present invention comprises substantially the same peaks at diffraction angles (2θ) as shown in FIG. 6, and the X-ray powder diffraction data are shown in Table 6:

TABLE 6

| 2θ (°) | intensity % |
|---|---|
| 7.2 | 19.1 |
| 7.6 | 21.0 |
| 9.3 | 78.1 |
| 10.7 | 100.0 |
| 11.5 | 34.0 |
| 14.0 | 36.4 |
| 15.2 | 18.8 |
| 15.8 | 58.9 |
| 18.9 | 48.7 |
| 19.9 | 55.5 |
| 20.6 | 22.1 |
| 21.6 | 69.0 |
| 22.2 | 39.0 |
| 22.5 | 96.5 |
| 23.0 | 28.6 |
| 23.4 | 19.2 |
| 24.0 | 23.6 |
| 25.8 | 90.3 |
| 27.9 | 34.2 |
| 31.7 | 27.1 |

The present invention provides a crystal form III of the sulfate salt of the compound of formula I having an X-ray powder diffraction spectrum comprising peaks at diffraction angles (2θ) of 22.1±0.2°, 23.6±0.2°, 10.4±0.2° and 21.6±0.2°.

Preferably, the X-ray powder diffraction spectrum further comprises peaks at diffraction angles (2θ) of 24.0±0.2°, 12.7±0.2°, 8.0±0.2°, 25.7±0.2° and 14.6±0.2°.

More preferably, the X-ray powder diffraction spectrum further comprises peaks at diffraction angles (2θ) of 17.1±0.2°, 20.9±0.2°, 27.0±0.2°, 11.0±0.2°, 18.2±0.2° and 16.5±0.2°.

Most preferably, the X-ray powder diffraction spectrum of crystal form III of the sulfate salt of the compound of formula I according to the present invention comprises substantially the same peaks at diffraction angles (2θ) as shown in FIG. 7, and the X-ray powder diffraction data are shown in Table 7:

TABLE 7

| 2θ (°) | intensity % |
| --- | --- |
| 7.4 | 13.4 |
| 8.0 | 38.4 |
| 9.0 | 10.9 |
| 10.4 | 90.0 |
| 11.0 | 21.2 |
| 12.7 | 41.2 |
| 14.6 | 32.3 |
| 15.2 | 13.6 |
| 16.5 | 16.9 |
| 17.1 | 30.4 |
| 18.2 | 17.9 |
| 19.2 | 13.7 |
| 20.9 | 25.6 |
| 21.6 | 83.6 |
| 22.1 | 100.0 |
| 23.6 | 97.7 |
| 24.0 | 81.3 |
| 25.7 | 33.2 |
| 27.0 | 23.9 |
| 29.4 | 16.7 |

The present invention provides a crystal form IV of the sulfate salt of the compound of formula I having an X-ray powder diffraction spectrum comprising peaks at diffraction angles (2θ) of 20.0±0.2°, 6.8±0.2°, 9.3±0.2° and 23.2±0.2°.

Preferably, the X-ray powder diffraction spectrum further comprises peaks at diffraction angles (2θ) of 25.2±0.2°, 22.5±0.2°, 17.7±0.2°, 20.5±0.2° and 14.9±0.2°.

More preferably, the X-ray powder diffraction spectrum further comprises peaks at diffraction angles (2θ) of 14.4±0.2°, 24.2±0.2°, 17.4±0.2°, 26.3±0.2°, 16.9±0.2° and 14.2±0.2°.

Most preferably, the X-ray powder diffraction spectrum of crystal form IV of the sulfate salt of the compound of formula I according to the present invention comprises substantially the same peaks at diffraction angles (2θ) as shown in FIG. 8, and the X-ray powder diffraction data are shown in Table 8:

TABLE 8

| 2θ (°) | intensity % |
| --- | --- |
| 6.8 | 92.7 |
| 9.3 | 74.4 |
| 14.2 | 32.6 |
| 14.4 | 48.9 |
| 14.9 | 51.2 |
| 16.2 | 25.5 |
| 16.9 | 33.1 |
| 17.4 | 43.4 |
| 17.7 | 59.3 |
| 18.2 | 23.1 |
| 20.0 | 100.0 |
| 20.5 | 52.1 |
| 22.5 | 59.6 |
| 23.2 | 63.6 |
| 24.2 | 45.4 |
| 25.2 | 59.9 |
| 25.5 | 27.3 |
| 26.3 | 37.9 |
| 28.0 | 26.8 |
| 30.2 | 23.3 |

In a still further preferred embodiment, the present invention provides a crystal form I of a phosphate salt of the compound of formula I having an X-ray powder diffraction spectrum comprising peaks at diffraction angles (2θ) of 22.6±0.2°, 10.7±0.2°, 21.6±0.2° and 17.8±0.2°.

Preferably, the X-ray powder diffraction spectrum further comprises peaks at diffraction angles (2θ) of 24.4±0.2°, 13.3±0.2°, 15.3±0.2°, 12.8±0.2° and 20.1±0.2°.

More preferably, the X-ray powder diffraction spectrum further comprises peaks at diffraction angles (2θ) of 14.4±0.2°, 20.6±0.2°, 25.4±0.2°, 19.2±0.2°, 10.1±0.2° and 12.3±0.2°.

Most preferably, the X-ray powder diffraction spectrum of crystal form I of the phosphate salt of the compound of formula I according to the present invention comprises substantially the same peaks at diffraction angles (2θ) as shown in FIG. 9, and the X-ray powder diffraction data are shown in Table 9:

TABLE 9

| 2θ (°) | intensity % |
| --- | --- |
| 10.1 | 19.8 |
| 10.7 | 80.4 |
| 12.0 | 14.1 |
| 12.3 | 19.6 |
| 12.8 | 26.5 |
| 13.3 | 31.6 |
| 14.4 | 24.0 |
| 15.3 | 28.0 |
| 15.6 | 18.6 |
| 16.7 | 18.0 |
| 17.8 | 56.2 |
| 19.2 | 19.9 |
| 20.1 | 26.0 |
| 20.6 | 22.3 |
| 21.6 | 56.8 |
| 22.6 | 100.0 |
| 23.4 | 18.3 |
| 24.4 | 40.7 |
| 25.4 | 20.0 |
| 26.3 | 13.1 |

In a still further preferred embodiment, the present invention provides a mesylate salt polymorph of the compound of formula I. The mesylate salt polymorph comprises six crystal forms, referred to as crystal form I, crystal form II, crystal form III, crystal form IV, crystal form V and crystal form VI of the mesylate salt, respectively.

The present invention provides a crystal form I of the mesylate salt of the compound of formula I having an X-ray powder diffraction spectrum comprising peaks at diffraction angles (2θ) of 19.1±0.2°, 25.6±0.2°, 15.0±0.2° and 25.0±0.2°.

Preferably, the X-ray powder diffraction spectrum further comprises peaks at diffraction angles (2θ) of 20.5±0.2°, 10.2±0.2°, 19.7±0.2°, 24.4±0.2° and 23.0±0.2°.

More preferably, the X-ray powder diffraction spectrum further comprises peaks at diffraction angles (2θ) of 9.4±0.2°, 16.3±0.2°, 17.4±0.2°, 8.6±0.2°, 21.2±0.2° and 22.6±0.2°.

Most preferably, the X-ray powder diffraction spectrum of crystal form I of the mesylate salt of the compound of formula I according to the present invention comprises substantially the same peaks at diffraction angles (2θ) as shown in FIG. 10, and the X-ray powder diffraction data are shown in Table 10:

TABLE 10

| 2θ (°) | intensity % |
| --- | --- |
| 6.8 | 19.6 |
| 8.6 | 29.9 |
| 9.4 | 43.1 |
| 10.2 | 59.9 |
| 15.0 | 75.7 |
| 16.3 | 41.1 |
| 16.9 | 24.0 |

TABLE 10-continued

| 2θ (°) | intensity % |
|---|---|
| 17.4 | 30.7 |
| 17.9 | 22.3 |
| 19.1 | 100.0 |
| 19.7 | 58.6 |
| 20.5 | 66.8 |
| 21.2 | 28.2 |
| 22.6 | 26.5 |
| 23.0 | 48.6 |
| 24.4 | 52.9 |
| 25.0 | 68.8 |
| 25.6 | 79.3 |
| 27.6 | 20.9 |
| 32.4 | 20.7 |

The present invention provides a crystal form II of the mesylate salt of the compound of formula I having an X-ray powder diffraction spectrum comprising peaks at diffraction angles (2θ) of 24.3±0.2°, 20.1±0.2°, 11.0±0.2° and 20.6±0.2°.

Preferably, the X-ray powder diffraction spectrum further comprises peaks at diffraction angles (2θ) of 17.4±0.2°, 22.7±0.2°, 23.8±0.2°, 12.1±0.2° and 15.7±0.2°.

More preferably, the X-ray powder diffraction spectrum further comprises peaks at diffraction angles (2θ) of 8.7±0.2°, 16.7±0.2°, 15.1±0.2, 18.5±0.2°, 17.7±0.2° and 6.5±0.2°.

Most preferably, the X-ray powder diffraction spectrum of crystal form II of the mesylate salt of the compound of formula I according to the present invention comprises substantially the same peaks at diffraction angles (2θ) as shown in FIG. 11, and the X-ray powder diffraction data are shown in Table 11:

TABLE 11

| 2θ (°) | intensity % |
|---|---|
| 6.5 | 11.6 |
| 7.0 | 10.2 |
| 8.7 | 22.9 |
| 11.0 | 41.4 |
| 12.1 | 25.2 |
| 12.7 | 7.6 |
| 15.1 | 21.4 |
| 15.7 | 23.2 |
| 16.7 | 22.6 |
| 17.4 | 39.4 |
| 17.7 | 15.7 |
| 18.5 | 19.9 |
| 20.1 | 52.0 |
| 20.6 | 39.5 |
| 22.7 | 38.1 |
| 23.8 | 37.3 |
| 24.3 | 100.0 |
| 26.8 | 7.5 |
| 32.8 | 8.2 |
| 40.6 | 9.5 |

The present invention provides a crystal form III of the mesylate salt of the compound of formula I having an X-ray powder diffraction spectrum comprising peaks at diffraction angles (2θ) of 24.5±0.2°, 22.6±0.2°, 6.1±0.2° and 18.8±0.2°.

Preferably, the X-ray powder diffraction spectrum further comprises peaks at diffraction angles (2θ) of 15.7±0.2°, 11.7±0.2°, 21.3±0.2°, 23.8±0.2° and 8.4±0.2°.

More preferably, the X-ray powder diffraction spectrum further comprises peaks at diffraction angles (2θ) of 16.7±0.2°, 17.3±0.2°, 9.4±0.2°, 15.3±0.2°, 22.0±0.2° and 12.2±0.2°.

Most preferably, the X-ray powder diffraction spectrum of crystal form III of the mesylate salt of the compound of formula I according to the present invention comprises substantially the same peaks at diffraction angles (2θ) as shown in FIG. 12, and the X-ray powder diffraction data are shown in Table 12:

TABLE 12

| 2θ (°) | intensity % |
|---|---|
| 6.1 | 68.4 |
| 8.4 | 27.4 |
| 9.4 | 24.8 |
| 11.7 | 50.3 |
| 12.2 | 17.9 |
| 13.7 | 14.8 |
| 15.3 | 22.8 |
| 15.7 | 50.5 |
| 16.7 | 25.1 |
| 17.3 | 25.1 |
| 18.4 | 12.2 |
| 18.8 | 50.9 |
| 21.3 | 44.0 |
| 22.0 | 18.8 |
| 22.6 | 77.7 |
| 23.8 | 30.1 |
| 24.5 | 100.0 |
| 27.2 | 14.6 |
| 28.7 | 15.5 |
| 30.3 | 12.1 |

The present invention provides a crystal form IV of the mesylate salt of the compound of formula I having an X-ray powder diffraction spectrum comprising peaks at diffraction angles (2θ) of 21.0±0.2°, 18.0±0.2°, 25.1±0.2° and 13.6±0.2°.

Preferably, the X-ray powder diffraction spectrum further comprises peaks at diffraction angles (2θ) of 21.4±0.2°, 22.6±0.2°, 19.9±0.2°, 19.1±0.2° and 10.4±0.2°.

More preferably, the X-ray powder diffraction spectrum further comprises peaks at diffraction angles (2θ) of 30.4±0.2°, 33.5±0.2°, 12.4±0.2°, 31.7±0.2°, 17.5±0.2° and 8.3±0.2°.

Most preferably, the X-ray powder diffraction spectrum of crystal form IV of the mesylate salt of the compound of formula I according to the present invention comprises substantially the same peaks at diffraction angles (2θ) as shown in FIG. 13, and the X-ray powder diffraction data are shown in Table 13:

TABLE 13

| 2θ (°) | intensity % |
|---|---|
| 8.3 | 29.1 |
| 10.4 | 44.2 |
| 12.4 | 31.0 |
| 13.6 | 68.6 |
| 16.8 | 27.6 |
| 17.5 | 29.8 |
| 18.0 | 91.9 |
| 19.1 | 46.6 |
| 19.9 | 51.9 |
| 21.0 | 100.0 |
| 21.4 | 65.6 |
| 22.6 | 63.3 |
| 23.9 | 24.8 |
| 25.1 | 77.1 |
| 25.5 | 24.4 |
| 30.4 | 36.5 |
| 31.7 | 30.7 |
| 33.5 | 34.9 |
| 34.2 | 27.4 |
| 37.0 | 27.7 |

The present invention provides a crystal form V of the mesylate salt of the compound of formula I having an X-ray powder diffraction spectrum comprising peaks at diffraction angles (2θ) of 24.6±0.2°, 23.3±0.2°, 14.9±0.2° and 20.1±0.2°.

Preferably, the X-ray powder diffraction spectrum further comprises peaks at diffraction angles (2θ) of 22.9±0.2°, 10.9±0.2°, 17.0±0.2°, 25.7±0.2° and 13.9±0.2°.

More preferably, the X-ray powder diffraction spectrum further comprises peaks at diffraction angles (2θ) of 15.3±0.2°, 27.0±0.2°, 30.5±0.2°, 18.7±0.2°, 20.6±0.2° and 21.9±0.2°.

Most preferably, the X-ray powder diffraction spectrum of crystal form V of the mesylate salt of the compound of formula I according to the present invention comprises substantially the same peaks at diffraction angles (2θ) as shown in FIG. 14, and the X-ray powder diffraction data are shown in Table 14:

TABLE 14

| 2θ (°) | intensity % |
|---|---|
| 8.4 | 15.0 |
| 9.4 | 20.6 |
| 10.9 | 51.1 |
| 13.9 | 41.0 |
| 14.9 | 58.2 |
| 15.3 | 27.9 |
| 15.9 | 14.1 |
| 17.0 | 45.1 |
| 18.7 | 25.0 |
| 20.1 | 53.8 |
| 20.6 | 23.3 |
| 21.9 | 22.2 |
| 22.9 | 52.5 |
| 23.3 | 78.9 |
| 24.6 | 100.0 |
| 25.7 | 44.0 |
| 27.0 | 26.9 |
| 30.5 | 26.9 |
| 39.3 | 22.0 |
| 39.8 | 17.4 |

The present invention provides a crystal form VI of the mesylate salt of the compound of formula I having an X-ray powder diffraction spectrum comprising peaks at diffraction angles (2θ) of 11.7±0.2°, 19.8±0.2°, 17.2±0.2° and 6.8±0.2°.

Preferably, the X-ray powder diffraction spectrum further comprises peaks at diffraction angles (2θ) of 23.6±0.2°, 22.6±0.2°, 25.5±0.2°, 24.2±0.2° and 23.2±0.2°.

More preferably, the X-ray powder diffraction spectrum further comprises peaks at diffraction angles (2θ) of 18.9±0.2°, 18.6±0.2°, 22.4±0.2°, 14.1±0.2°, 24.6±0.2° and 10.9±0.2°.

Most preferably, the X-ray powder diffraction spectrum of crystal form VI of the mesylate salt of the compound of formula I according to the present invention comprises substantially the same peaks at diffraction angles (2θ) as shown in FIG. 15, and the X-ray powder diffraction data are shown in Table 15:

TABLE 15

| 2θ (°) | intensity % |
|---|---|
| 6.8 | 63.4 |
| 7.9 | 23.2 |
| 8.7 | 34.0 |
| 10.9 | 34.1 |
| 11.7 | 100.0 |
| 12.6 | 34.0 |

TABLE 15-continued

| 2θ (°) | intensity % |
|---|---|
| 14.1 | 38.3 |
| 17.2 | 80.9 |
| 17.8 | 26.7 |
| 18.6 | 42.8 |
| 18.9 | 44.8 |
| 19.8 | 91.7 |
| 22.0 | 33.6 |
| 22.4 | 38.6 |
| 22.6 | 51.7 |
| 23.2 | 45.7 |
| 23.6 | 55.8 |
| 24.2 | 48.0 |
| 24.6 | 36.8 |
| 25.5 | 49.9 |

In a still further preferred embodiment, the present invention provides a fumarate salt polymorph of the compound of formula I. The fumarate salt polymorph comprises two crystal forms, referred to as crystal form I and crystal form II of the fumarate salt, respectively.

The present invention provides a crystal form I of the fumarate salt of the compound of formula I having an X-ray powder diffraction spectrum comprising peaks at diffraction angles (2θ) of 7.1±0.2°, 12.0±0.2°, 14.9±0.2° and 17.1±0.2°.

Preferably, the X-ray powder diffraction spectrum further comprises peaks at diffraction angles (2θ) of 19.1±0.2°, 23.4±0.2°, 23.7±0.2°, 26.6±0.2° and 28.7±0.2°.

More preferably, the X-ray powder diffraction spectrum further comprising peaks at diffraction angles (2θ) of 25.2±0.2°, 10.5±0.2°, 25.6±0.2°, 38.7±0.2°, 13.3±0.2° and 7.8±0.2°.

Most preferably, the X-ray powder diffraction spectrum of crystal form I of the fumarate salt of the compound of formula I according to the present invention comprises substantially the same peaks at diffraction angles (2θ) as shown in FIG. 16, and the X-ray powder diffraction data are shown in Table 16:

TABLE 16

| 2θ (°) | intensity % |
|---|---|
| 7.1 | 100.0 |
| 7.8 | 7.7 |
| 10.5 | 13.7 |
| 12.0 | 94.6 |
| 13.3 | 8.5 |
| 14.9 | 80.7 |
| 17.1 | 62.2 |
| 19.1 | 49.7 |
| 19.8 | 6.0 |
| 21.2 | 6.7 |
| 23.4 | 41.0 |
| 23.7 | 36.6 |
| 25.2 | 15.1 |
| 25.6 | 12.9 |
| 26.6 | 27.2 |
| 28.7 | 23.4 |
| 30.1 | 5.5 |
| 30.3 | 5.8 |
| 30.5 | 7.6 |
| 38.7 | 9.0 |

The present invention provides a crystal form II of the fumarate salt of the compound of formula I having an X-ray powder diffraction spectrum comprising peaks at diffraction angles (2θ) of 6.0±0.2°, 22.7±0.2°, 25.1±0.2° and 23.3±0.2°.

Preferably, the X-ray powder diffraction spectrum further comprises peaks at diffraction angles (2θ) of 16.9±0.2°, 25.5±0.2°, 24.2±0.2°, 8.8±0.2° and 11.9±0.2°.

More preferably, the X-ray powder diffraction spectrum further comprises peaks at diffraction angles (2θ) of 20.5±0.2°, 29.5±0.2°, 8.3±0.2°, 19.9±0.2°, 13.7±0.2° and 37.6±0.2°.

Most preferably, the X-ray powder diffraction spectrum of crystal form II of the fumarate salt of the compound of formula I according to the present invention comprises substantially the same peaks at diffraction angles (2θ) as shown in FIG. 17, and the X-ray powder diffraction data are shown in Table 17:

TABLE 17

| 2θ (°) | intensity % |
|---|---|
| 6.0 | 100.0 |
| 8.3 | 21.9 |
| 8.8 | 50.2 |
| 11.9 | 49.0 |
| 13.7 | 19.8 |
| 14.3 | 17.7 |
| 16.9 | 56.7 |
| 17.7 | 18.2 |
| 18.2 | 13.6 |
| 19.9 | 20.2 |
| 20.5 | 34.4 |
| 21.6 | 15.2 |
| 22.7 | 75.3 |
| 23.3 | 58.9 |
| 24.2 | 54.5 |
| 25.1 | 59.6 |
| 25.5 | 56.4 |
| 29.5 | 25.9 |
| 34.5 | 13.5 |
| 37.6 | 18.6 |

In a still further preferred embodiment, the present invention provides a maleate salt polymorph of the compound of formula I. The maleate salt polymorph comprises three crystal forms, referred to as crystal form I, crystal form II and crystal form III of the maleate salt, respectively.

The present invention provides a crystal form I of the maleate salt of the compound of formula I having an X-ray powder diffraction spectrum comprising peaks at diffraction angles (2θ) of 7.9±0.2°, 24.6±0.2°, 7.5±0.2° and 18.2±0.2°.

Preferably, the X-ray powder diffraction spectrum further comprises peaks at diffraction angles (2θ) of 7.2±0.2°, 22.5±0.2°, 14.5±0.2°, 25.4±0.2° and 21.0±0.2°.

More preferably, the X-ray powder diffraction spectrum further comprises peaks at diffraction angles (2θ) of 19.7±0.2°, 13.0±0.2°, 15.1±0.2°, 19.1±0.2°, 22.0±0.2° and 11.7±0.2°.

Most preferably, the X-ray powder diffraction spectrum of crystal form I of the maleate salt of the compound of formula I according to the present invention comprises substantially the same peaks at diffraction angles (2θ) as shown in FIG. 18, and the X-ray powder diffraction data are shown in Table 18:

TABLE 18

| 2θ (°) | intensity % |
|---|---|
| 7.2 | 69.5 |
| 7.5 | 88.8 |
| 7.9 | 100.0 |
| 11.7 | 26.4 |
| 13.0 | 31.9 |
| 14.1 | 26.0 |
| 14.5 | 56.2 |
| 15.1 | 30.2 |
| 15.9 | 25.7 |

TABLE 18-continued

| 2θ (°) | intensity % |
|---|---|
| 18.2 | 71.5 |
| 19.1 | 27.3 |
| 19.7 | 39.5 |
| 21.0 | 45.4 |
| 22.0 | 26.6 |
| 22.5 | 61.6 |
| 23.3 | 24.5 |
| 23.6 | 22.7 |
| 24.6 | 97.6 |
| 25.4 | 54.5 |
| 27.2 | 24.8 |

The present invention provides a crystal form II of the maleate salt of the compound of formula I having an X-ray powder diffraction spectrum comprising peaks at diffraction angles (2θ) of 20.3±0.2°, 24.9±0.2°, 23.4±0.2° and 16.8±0.2°.

Preferably, the X-ray powder diffraction spectrum further comprises peaks at diffraction angles (2θ) of 7.2±0.2°, 18.6±0.2°, 21.0±0.2°, 10.1±0.2° and 9.8±0.2°.

More preferably, the X-ray powder diffraction spectrum further comprises peaks at diffraction angles (2θ) of 25.5±0.2°, 13.6±0.2°, 18.3±0.2°, 12.5±0.2°, 21.6±0.2° and 15.4±0.2°.

Most preferably, the X-ray powder diffraction spectrum of crystal form II of the maleate salt of the compound of formula I according to the present invention comprises substantially the same peaks at diffraction angles (2θ) as shown in FIG. 19, and the X-ray powder diffraction data are shown in Table 19:

TABLE 19

| 2θ (°) | intensity % |
|---|---|
| 7.2 | 43.4 |
| 9.8 | 27.5 |
| 10.1 | 31.6 |
| 12.5 | 21.3 |
| 12.9 | 9.9 |
| 13.6 | 24.5 |
| 15.4 | 19.5 |
| 15.9 | 11.5 |
| 16.8 | 44.5 |
| 18.3 | 21.5 |
| 18.6 | 38.3 |
| 20.3 | 100.0 |
| 21.0 | 38.1 |
| 21.6 | 21.3 |
| 22.5 | 12.0 |
| 23.4 | 55.6 |
| 24.9 | 56.0 |
| 25.5 | 27.0 |
| 26.7 | 11.2 |
| 27.2 | 13.0 |

The present invention provides a crystal form III of the maleate salt of the compound of formula I having an X-ray powder diffraction spectrum comprising peaks at diffraction angles (2θ) of 21.6±0.2°, 22.4±0.2°, 17.9±0.2° and 25.8±0.2°.

Preferably, the X-ray powder diffraction spectrum further comprises peaks at diffraction angles (2θ) of 7.7±0.2°, 23.4±0.2°, 24.4±0.2°, 11.9±0.2° and 26.6±0.2°.

More preferably, the X-ray powder diffraction spectrum further comprises peaks at diffraction angles (2θ) of 16.4±0.2°, 15.4±0.2°, 17.6±0.2°, 12.4±0.2°, 19.7±0.2° and 21.2±0.2°.

Most preferably, the X-ray powder diffraction spectrum of crystal form III of the maleate salt of the compound of formula I according to the present invention comprises substantially the same peaks at diffraction angles (2θ) as shown in FIG. 20, and the X-ray powder diffraction data are shown in Table 20:

TABLE 20

| 2θ (°) | intensity % |
| --- | --- |
| 7.7 | 73.4 |
| 11.9 | 47.4 |
| 12.4 | 34.8 |
| 14.7 | 27.4 |
| 15.4 | 42.7 |
| 16.4 | 43.5 |
| 16.8 | 26.9 |
| 17.6 | 36.6 |
| 17.9 | 82.5 |
| 19.7 | 33.3 |
| 21.2 | 32.9 |
| 21.6 | 100.0 |
| 22.4 | 89.9 |
| 23.1 | 30.7 |
| 23.4 | 72.1 |
| 24.4 | 62.1 |
| 25.8 | 77.2 |
| 26.6 | 44.0 |
| 28.2 | 32.0 |
| 30.2 | 22.6 |

In a still further preferred embodiment, the present invention provides an acetate salt polymorph of the compound of formula I. The acetate salt polymorph comprises two crystal forms, referred to as crystal form I and crystal form II of the acetate salt, respectively.

The present invention provides a crystal form I of the acetate salt of the compound of formula I having an X-ray powder diffraction spectrum comprising peaks at diffraction angles (2θ) of 23.0±0.2°, 11.8±0.2°, 16.3±0.2° and 7.4±0.2°.

Preferably, the X-ray powder diffraction spectrum further comprises peaks at diffraction angles (2θ) of 22.5±0.2°, 13.0±0.2°, 14.9±0.2°, 13.4±0.2° and 6.5±0.2°.

More preferably, the X-ray powder diffraction spectrum further comprising peaks at diffraction angles (2θ) of 29.3±0.2°, 12.4±0.2°, 20.1±0.2°, 9.7±0.2°, 24.0±0.2° and 28.0±0.2°.

Most preferably, the X-ray powder diffraction spectrum of crystal form I of the acetate salt of the compound of formula I according to the present invention comprises substantially the same peaks at diffraction angles (2θ) as shown in FIG. 21, and the X-ray powder diffraction data are shown in Table 21:

TABLE 21

| 2θ (°) | intensity % |
| --- | --- |
| 6.5 | 23.8 |
| 7.4 | 56.4 |
| 9.7 | 21.4 |
| 10.3 | 15.4 |
| 11.8 | 72.8 |
| 12.4 | 21.6 |
| 13.0 | 32.8 |
| 13.4 | 26.0 |
| 14.2 | 13.6 |
| 14.9 | 29.6 |
| 16.3 | 67.3 |
| 17.8 | 16.5 |
| 20.1 | 21.5 |
| 20.5 | 17.0 |
| 22.5 | 56.0 |
| 23.0 | 100.0 |
| 24.0 | 18.0 |

TABLE 21-continued

| 2θ (°) | intensity % |
| --- | --- |
| 28.0 | 17.8 |
| 29.3 | 23.7 |

The present invention provides a crystal form II of the acetate salt of the compound of formula I having an X-ray powder diffraction spectrum comprising peaks at diffraction angles (2θ) of 8.4±0.2°, 19.9±0.2°, 23.0±0.2° and 24.8±0.2°.

Preferably, the X-ray powder diffraction spectrum further comprises peaks at diffraction angles (2θ) of 24.4±0.2°, 16.9±0.2°, 13.9±0.2°, 19.6±0.2° and 11.0±0.2°.

More preferably, the X-ray powder diffraction spectrum further comprises peaks at diffraction angles (2θ) of 6.4±0.2°, 17.8±0.2°, 24.1±0.2°, 9.7±0.2°, 11.9±0.2° and 26.6±0.2°.

Most preferably, the X-ray powder diffraction spectrum of crystal form II of the acetate salt of the compound of formula I according to the present invention comprises substantially the same peaks at diffraction angles (2θ) as shown in FIG. 22, and the X-ray powder diffraction data are shown in Table 22:

TABLE 22

| 2θ (°) | intensity % |
| --- | --- |
| 6.4 | 35.2 |
| 8.4 | 100.0 |
| 9.7 | 25.4 |
| 11.0 | 37.3 |
| 11.9 | 21.1 |
| 13.9 | 41.4 |
| 16.9 | 45.9 |
| 17.8 | 34.3 |
| 18.8 | 17.7 |
| 19.6 | 40.3 |
| 19.9 | 68.4 |
| 20.8 | 13.6 |
| 22.0 | 16.0 |
| 23.0 | 64.3 |
| 23.7 | 14.8 |
| 24.1 | 26.7 |
| 24.4 | 50.9 |
| 24.8 | 57.1 |
| 26.6 | 18.9 |
| 30.4 | 18.3 |

The term "substantially the same" related to X-ray diffraction peak position as used herein means to consider the typical peak position and intensity variability. For example, those skilled in the art will understand that the measured values of the peak positions (2θ) will be changed due to the different XRPD instruments, and sometimes this change may reach up to 0.2°. Moreover, those skilled in the art will understand that the preparation method of the XRPD sample, the XRPD instruments, the crystallinity of the sample, the sample amount, the preferred orientation of the crystal and other factors will cause a change of relative peak intensity of the sample in the XRPD spectrum.

In another aspect, the present invention provides a method for preparing the free base polymorph, the acid salt or the acid salt polymorph of the compound of formula I. The method for preparing the free base polymorph is selected from the following preparation methods:

Method 1: step 1: dissolving the free base of the compound of formula I in an aqueous solvent, an organic solvent or a mixed solvent; step 2: cooling the solution to precipitate the polymorph, or adding an anti-solvent to the clear solution of the compound to precipitate the polymorph, or evaporating the clear solution of the compound slowly, or adding an original compound solid or other solid particle additive as a heteronuclear crystal seed to the solution of the compound to induce the polymorph;

Method 2: dispersing the compound in an aqueous solvent, an organic solvent or a mixed solvent, or in an atmosphere of these media to obtain the polymorph; and Method 3: combining method 1 and method 2 to obtain the free base polymorph. The method for preparing the acid salt polymorph of the compound of formula I comprises the following steps of:

Step 1: preparing the acid salt of the compound of formula I, the specific steps being as follows: dissolving or dispersing the free base of the compound in an aqueous solvent or a suitable organic solvent, and then adding a liquid or solid or solution of inorganic acid or organic acid to the above system to prepare the acid salt of the compound of formula I; or, adding the free base solid to an acid solution to prepare the acid salt of the compound of formula I; and Step 2: preparing the acid salt polymorph of the compound of formula I in accordance with the above method for preparing the free base polymorph.

In a further preferred embodiment, the organic solvent comprises, but is not limited to, the solvents listed below, for example, methanol, ethanol, isopropanol, acetonitrile, acetone, ethyl acetate, isopropyl acetate, toluene, n-butanol, cyclohexane, dichloromethane, dimethylformamide, dimethylacetamide, dimethyl sulfoxide, dioxane, ethyl ether, n-heptane, n-hexane, methyl ethyl ketone, isooctane, pentane, dipropanol, tetrahydrofuran, dimethyl tetrahydrofuran, trichloroethane, dimethylbenzene or a mixture thereof. Other solvents can be supercritical fluids, such as carbon dioxide liquids, ionic liquids, polymer solutions, and the like.

In another aspect, the present invention provides a pharmaceutical composition comprising a therapeutically effective amount of the above free base or acid salt polymorph of the compound of formula I and a pharmaceutically acceptable carrier.

In another aspect, the present invention provides a use of the above free base or acid salt polymorph of the compound of formula I, or the above pharmaceutical composition in the preparation of a medicament for treating a disease mediated by the activity of an EGFR mutant or the activity of a mutant activated by exon 19 deletion.

Preferably, the EGFR mutant is selected from the group consisting of EGFR-L858R mutant and EGFR-T790M.

More preferably, the disease mediated by the activity of an EGFR mutant comprises a disease mediated alone or partially by the activity of an EGFR mutant.

In another aspect, the present invention provides a use of the above free base or acid salt polymorph of the compound of formula I, or the above pharmaceutical composition in the preparation of a medicament for treating cancer.

Preferably, the cancer is selected from the group consisting of ovarian cancer, cervical cancer, colorectal cancer, breast cancer, pancreatic cancer, glioma, glioblastoma, melanoma, prostate cancer, leukemia, lymphoma, non-Hodgkin lymphoma, gastric cancer, lung cancer, hepatocellular carcinoma, gastric cancer, gastrointestinal stromal tumor (GIST), thyroid cancer, cholangiocarcinoma, endometrial cancer, renal cancer, anaplastic large cell lymphoma, acute myeloid leukemia (AML), multiple myeloma, melanoma and mesothelioma.

More preferably, the cancer is non-small cell lung cancer.

PREFERRED EMBODIMENTS

1. Terms

Figure 1:
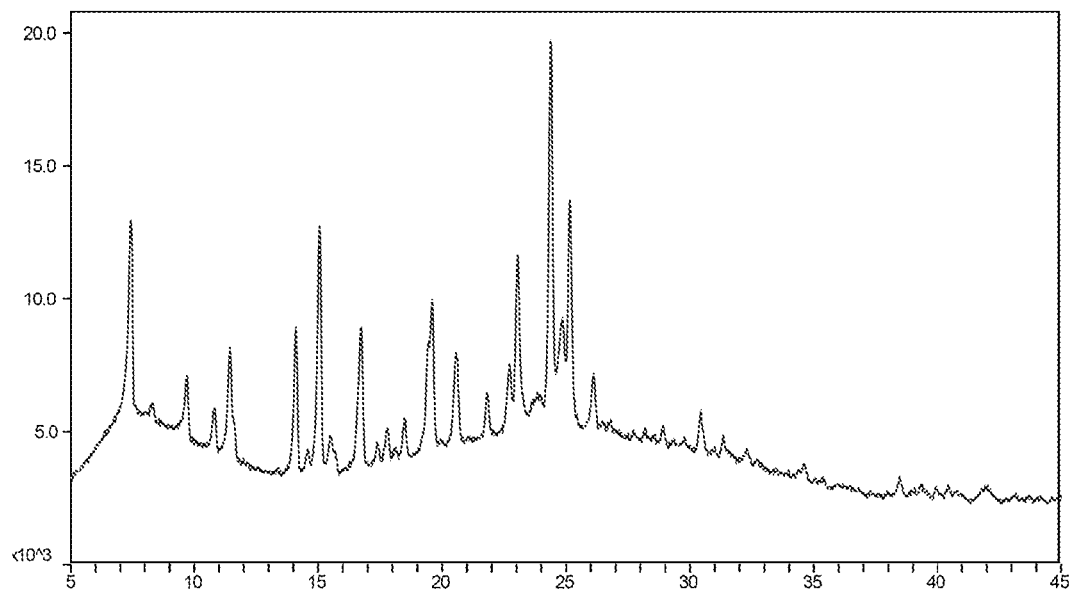
FIG. 1 is the X-ray powder diffraction spectrum of crystal form I of the free base of the compound of formula I.

The term "pharmaceutically acceptable" as used herein refers to those compounds, materials, compositions, and/or dosage forms which are, within the scope of sound medical judgment, suitable for contact with the tissues of human beings and animal without excessive toxicity, irritation, allergic reaction or other problematic complications, and are commensurate with a reasonable benefit to risk ratio.

The term "substantially pure" as used herein refers to, in certain preferred embodiments of the present invention, the crystalline structure of the compound of formula I being in substantially pure form, i.e., the HPLC purity or crystal form is substantially above 90% (including the number itself), preferably above 95%, more preferably above 98%, and most preferably above 99.5%.

The term "polymorphism" or "polymorph" as used herein refers to crystal forms having the same chemical composition but different spatial arrangement of the molecules, atoms, and/or ions forming the crystal. Although polymorphs have the same chemical composition, they differ in packing and geometric arrangement, and can exhibit different physical properties, such as melting point, shape, color, density, hardness, deformability, stability, solubility, dissolution rate and similar properties. Depending on their temperature-stability relationship, two polymorphs can be either monotropic or enantiotropic. For a monotropic system, the relative stability between the two solid phases remains constant as the temperature changes. In contrast, in an enantiotropic system, there is a transition temperature at which the stability of the two phases is reversed (Theory and Origin of Polymorphism in "Polymorphism in Pharmaceutical Solids" (1999) ISBN: )-8247-0237). The phenomenon of a compound existing in different crystal structures is called drug polymorphism phenomenon.

The crystalline structures of the present invention can be prepared by various methods, including crystallization or recrystallization from a suitable solvent, sublimation, growth from a melt, solid state transformation from another phase, crystallization from a supercritical fluid, jet spray, and the like. Techniques for crystallization or recrystallization of crystalline structures from a solvent mixture include solvent evaporation, decreasing the temperature of the solvent mixture, seeding in a supersaturated solvent mixture of the molecule and/or salt thereof, lyophilizing the solvent mixture, or adding an anti-solvent to the solvent mixture, and the like. Crystalline structures, including polymorphs, can be prepared using high-throughput crystallization techniques. Drug crystals including polymorphs, methods of preparation and characterization of drug crystals are disclosed in Solid-State Chemistry of Drugs, S. R. Byrn, R. R. Pfeiffer, and J. G. Stowell, 2nd, SSCI, West Lafayette, Ind., 1999.

In addition, as known to those skilled in the art, seed crystals are added to any crystallization mixture to promote crystallization. Thus, the present invention can also use seed crystals as a means of controlling the growth of a particular crystalline structure or as a means of controlling the particle size distribution of the crystalline product. Accordingly, as described in "Programmed cooling of batch crystallizers," J. W. Mullin and J. Nyvlt, Chemical Engineering Science, 1971, 26, 369-377, the calculation of the amount of seed crystal required depends on the size of the available seed crystal and the desired size of the average product particle. In general, small sized species are needed to effectively control the growth of crystals in the batch. Small sized seed crystals can be produced by sieving, milling, or micronizing of larger crystals, or by solution micro-crystallization. It should be noted that the milling or micronizing of the crystals cannot result in any change in the crystallinity of the desired crystal structure (i.e., change to amorphous or to another polymorph).

Crystal structures equivalent to the crystal structures disclosed or claimed in the present invention can exhibit similar but not identical analytical properties within a reasonable error range, depending on test conditions, purity, equipment, and other common variables known to those skilled in the art. Accordingly, it will be apparent to those skilled in the art that various modifications and variations can be made in the present invention without departing from the scope or spirit of the present invention. Other embodiments of the present invention will be apparent to those skilled in the art from consideration of the specification of the present invention disclosed herein and based on practice. Applicants intend that the specification and examples be considered as exemplary, but not as limiting the scope thereof.

As used herein, the term "room temperature" or "RT" refers to an ambient temperature of 20 to 25° C. (68-77° F.).

2. Experimental Materials

The reagents used in the examples of the present invention are commercially available industrial grade or analytical grade reagents. The selected compound of formula I is an amorphous solid which is prepared according to Example 26 of Patent Application PCT/CN2015/091189 filed by Hansoh.

3. Analytical Method 3.1 X-Ray Powder Diffraction

Those skilled in the art will recognize that an X-ray powder diffraction pattern can be obtained with a measurement error that depends on the measurement conditions used. In particular, it is generally known that the intensity in an X-ray powder diffraction pattern can fluctuate depending on the material conditions used. It should be further understood that the relative intensity can also vary depending on experimental conditions, and accordingly, the exact intensity should not be taken into account. In addition, a measurement error of a conventional X-ray powder diffraction angle is usually about 5% or less, and such degree of measurement error should be regarded as belonging to the diffraction angle described above. Therefore, it is to be understood that the crystal structures of the present invention are not limited to the crystal structures that provide X-ray diffraction spectra exactly the same as the X-ray powder diffraction spectra depicted in the Figures disclosed herein. Any crystal structures that provide X-ray powder diffraction spectra substantially the same as those disclosed in the Figures fall within the scope of the present invention. The ability to determine substantially the same X-ray powder diffraction spectra is within the ability of those skilled in the art. Other suitable standard calibrations are known to those skilled in the art. However, the relative intensity can vary depending on the size and shape of the crystal.

The polymorphs of the compound of formula I were characterized by their X-ray powder diffraction (XRPD) spectra. Therefore, the X-ray powder diffraction spectrum was collected by a Rigaku Uitimalv X-ray powder diffractometer using Cu Kα radiation (1.54 Å) in reflective mode. Tube voltage and current amount were set to 40 kV and 40 mA respectively. In the 2θ range of 5.0° to 45°, the sample was scanned for 5 minutes. All analysis was usually implemented at room temperature of 20° C.-30° C. The XRPD sample was prepared as follows: The sample was placed on a monocrystalline silicon wafer, then the sample powder was pressed by a glass sheet or an equivalent to ensure that the surface of the sample was flat and had a suitable height. Then, the sample holder was placed in the Rigaku Uitimalv instrument, and the X-ray powder diffraction spectrum was collected using the above instrument parameters. The measured difference related to the analysis result of the X-ray powder diffraction was produced by various factors including: (a) error in sample preparation (e.g., sample height), (b) the instrument error, (c) the calibration error, (d) operator error (including those errors that occur in the determination of peak positions), and (e) properties of the substance (e.g. preferred orientation error). Calibration error and sample height error often lead to shifts of all the peaks in the same direction. In general, the calibration factor will make the measured peak positions inconsistent with the expected peak positions and in the range of 2θ expected values ±0.2°.

Angle 2θ values (°) and intensity values (% relative to the highest peak value) of each polymorph obtained in the Examples of the present invention are shown in Tables 1 to 22.

3.2 Thermogravimetric Analysis (TGA)

Thermogravimetric analysis (TGA) experiments were performed on a TA Instruments™ model Q500. The sample (about 2-10 mg) was placed on a pre-weighed platinum pan. The sample weight was accurately measured by the instrument and recorded to a thousand of a milligram. The furnace was purged with nitrogen at 100 ml/min. Data were collected between room temperature and 300° C. at a heating rate of 10° C./min.

3.3. Differential Scanning Calorimetry (DSC)

Differential Scanning calorimetry (DSC) experiments were performed on a TA Instruments™ model Q200. The sample (about 2-10 mg) was weighed in an aluminum pan and accurately recorded to a hundred of a milligram and transferred to the DSC. The instrument was purged with nitrogen at 50 ml/min. Data were collected between room temperature to 300° C. at a heating rate of 10° C./min. The spectra were plotted when the endothermic peaks were downward. However, those skilled in the art will notice that in the DSC measurement, the measured start temperature and the maximum temperature vary in a certain degree, depending on the heating rate, crystal shape and purity, and other measured parameters.

The following specific examples are used to further describe the particular aspects of the solutions of the invention, but these examples are not intended to limit the scope of the invention in any way.

Example 1: Preparation of Crystal Form I of the Free Base of the Compound of Formula I About 20 mg of the free base solid of the compound of formula I (amorphous) were weighed and placed in a 1.5 mL vial, 100 μL of propanol as a positive solvent was added at each step, the mixture was shaken vertically and sonicated until the solid was completely dissolved, and then the addition of the positive solvent was stopped. Under stirring condition, water as an anti-solvent was slowly added at room temperature until a large amount of solid precipitated. After the precipitation stopped, stirring was continued for twenty minutes. A solid-liquid separation was carried out to obtain crystal form I of the free base of the compound of formual I. The X-ray powder diffraction spectrum is shown in FIG. 1.

Figure 2:
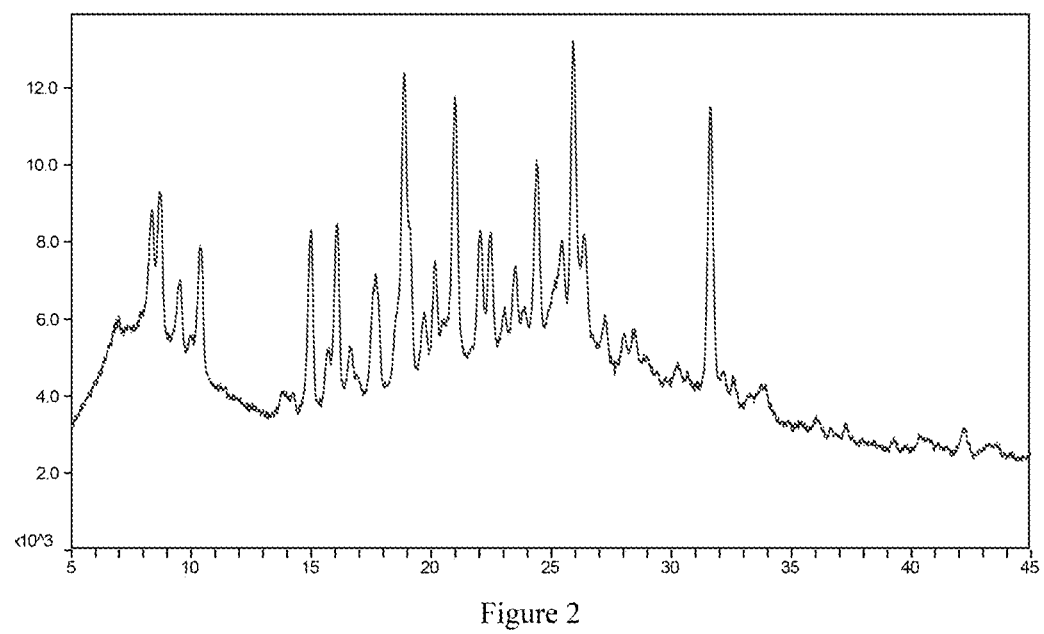
FIG. 2 is the X-ray powder diffraction spectrum of crystal form II of the free base of the compound of formula I.

Example 2: Preparation of Crystal Form II of the Free Base of the Compound of Formula I About 20 mg of the free base solid of the compound I of formula I (amorphous) were weighed and placed in a 1.5 mL vial, and then ethyl formate as a positive solvent was added. The mixture was shaken vertically, the solid was dissolved first and then quickly recrystallized to form a solid. A solid-liquid separation was carried out to obtain crystal form II of the free base of the compound of formual I. The X-ray powder diffraction spectrum is shown in FIG. 2.

Figure 3:
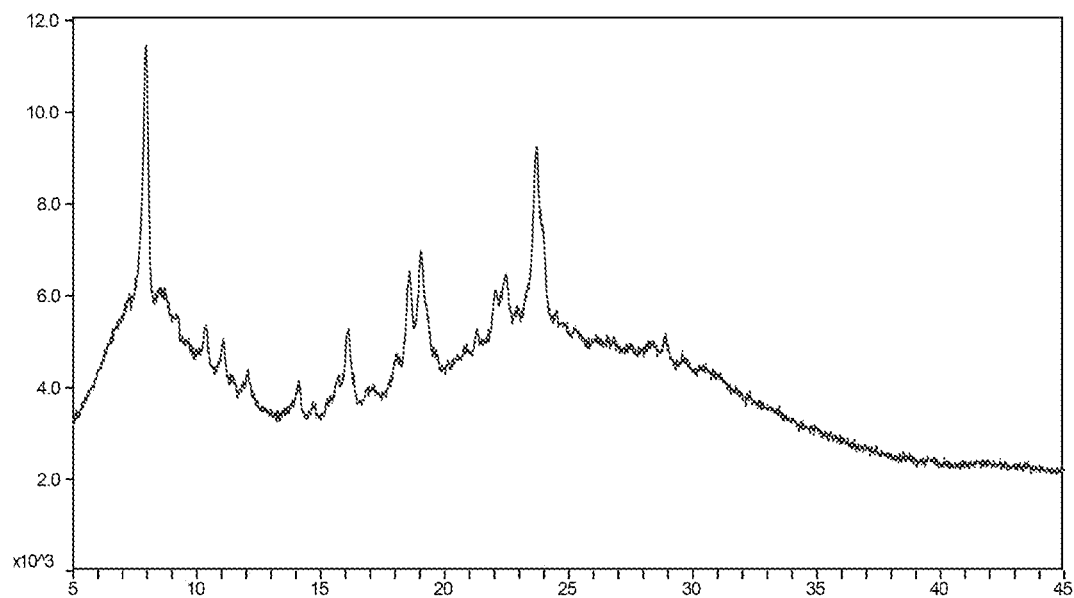
FIG. 3 is the X-ray powder diffraction spectrum of crystal form III of the free base of the compound of formula I.

Example 3: Preparation of Crystal Form III of the Free Base of the Compound of Formula I About 20 mg of the free base solid of the compound of formula I (amorphous) were weighed and placed in a 1.5 mL vial, 100 μL of methanol as a positive solvent was added at each step, the mixture was shaken vertically and sonicated until the solid was completely dissolved, and then the addition of the positive solvent was stopped. Under stirring conditions, water as an anti-solvent was slowly added at room temperature until a large amount of solid precipitated. After the precipitation stopped, stirring was continued for twenty minutes. A solid-liquid separation was carried out to obtain crystal form III of the free base of the compound of formual I. The X-ray powder diffraction spectrum is shown in FIG. 3.

Figure 4:
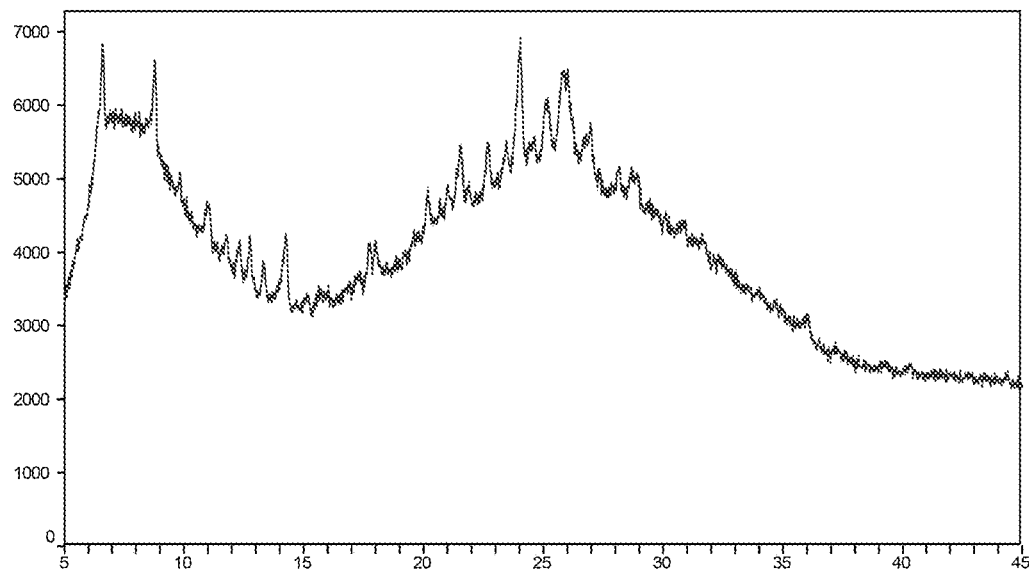
FIG. 4 is the X-ray powder diffraction spectrum of crystal form I of a hydrochloride salt of the compound of formula I.

Example 4: Preparation of Crystal Form I of a Hydrochloride Salt of the Compound of Formula I About 20 mg of the free base solid of the compound of formula I (amorphous) were weighed and placed in a 1.5 mL vial, and then 200 μL of acetonitrile as a positive solvent was added to dissolve the solid. Under stirring conditions, an equimolar amount of hydrochloric acid was added to the vial at room temperature. After stirring was continued for 24 hours, a solid-liquid separation was carried out to obtain crystal form I of the hydrochloride salt of the compound of formula I. The X-ray powder diffraction spectrum is shown in FIG. 4.

Figure 5:
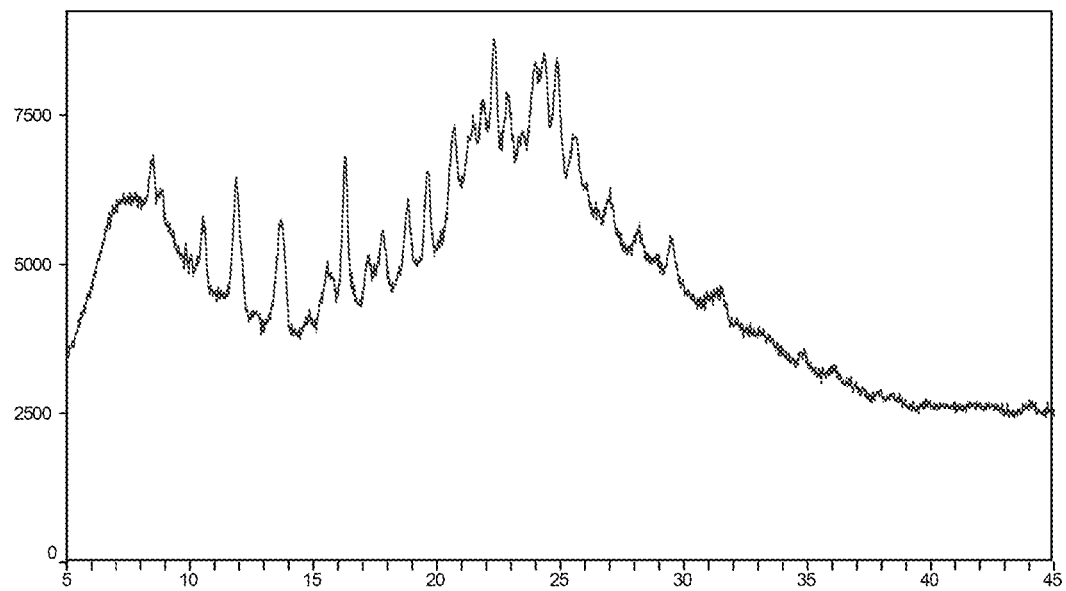
FIG. 5 is the X-ray powder diffraction spectrum of crystal form I of a sulfate salt of the compound of formula I.

Example 5: Preparation of Crystal Form I of a Sulfate Salt of the Compound of Formula I About 20 mg of the free base solid of the compound of formula I (amorphous) were weighed and placed in a 1.5 mL vial, and then 200 μL of methanol as a positive solvent were added to dissolve the solid. Under stirring conditions, an equimolar amount of sulfuric acid was added to the vial at room temperature. After stirring was continued for 24 hours, a solid-liquid separation was carried out to obtain crystal form I of the sulfate salt of the compound of formula I. The X-ray powder diffraction spectrum is shown in FIG. 5.

Figure 6:
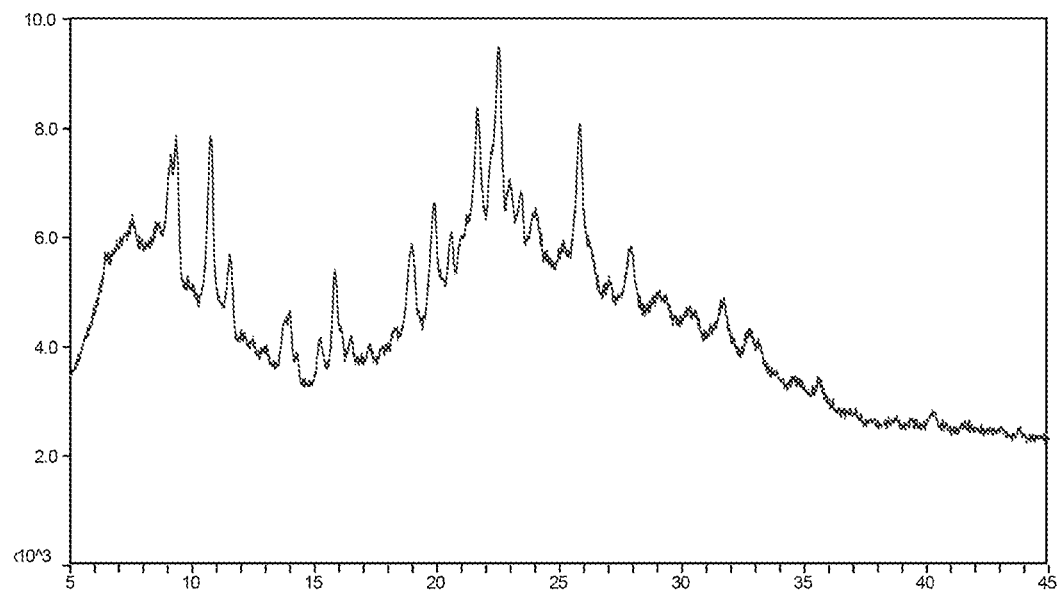
FIG. 6 is the X-ray powder diffraction spectrum of crystal form II of a sulfate salt of the compound of formula I.

Example 6: Preparation of Crystal Form II of a Sulfate Salt of the Compound of Formula I About 20 mg of the free base solid of the compound of formula I (amorphous) were weighed and placed in a 1.5 mL vial, and then 200 μL of acetonitrile as a positive solvent were added to dissolve the solid. Under stirring conditions, an equimolar amount of sulfuric acid was added to the vial at room temperature. After stirring was continued for 24 hours, a solid-liquid separation was carried out to obtain crystal form II of the sulfate salt of the compound of formula I. The X-ray powder diffraction spectrum is shown in FIG. 6.

Figure 7:
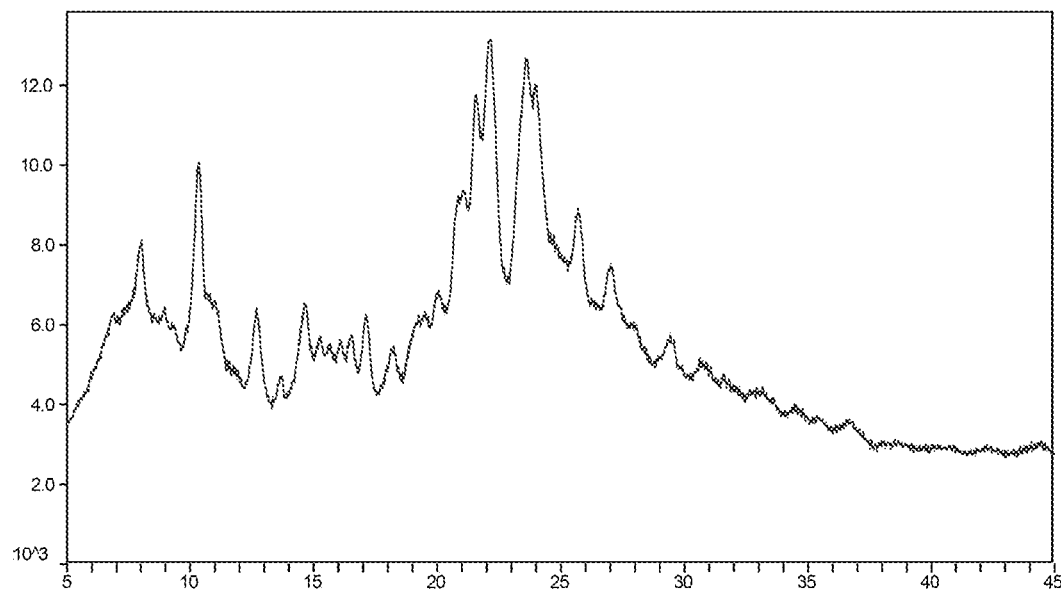
FIG. 7 is the X-ray powder diffraction spectrum of crystal form III of a sulfate salt of the compound of formula I.

Example 7: Preparation of Crystal Form III of a Sulfate Salt of the Compound of Formula I About 20 mg of the free base solid of the compound of formula I (amorphous) were weighed and placed in a 1.5 mL vial, and then 200 μL of acetone as a positive solvent were added to dissolve the solid. Under stirring conditions, an equimolar amount of sulfuric acid was added to the vial at room temperature. After stirring was continued for 24 hours, a solid-liquid separation was carried out to obtain crystal form III of the sulfate salt of the compound of formula I. The X-ray powder diffraction spectrum is shown in FIG. 7.

Figure 8:
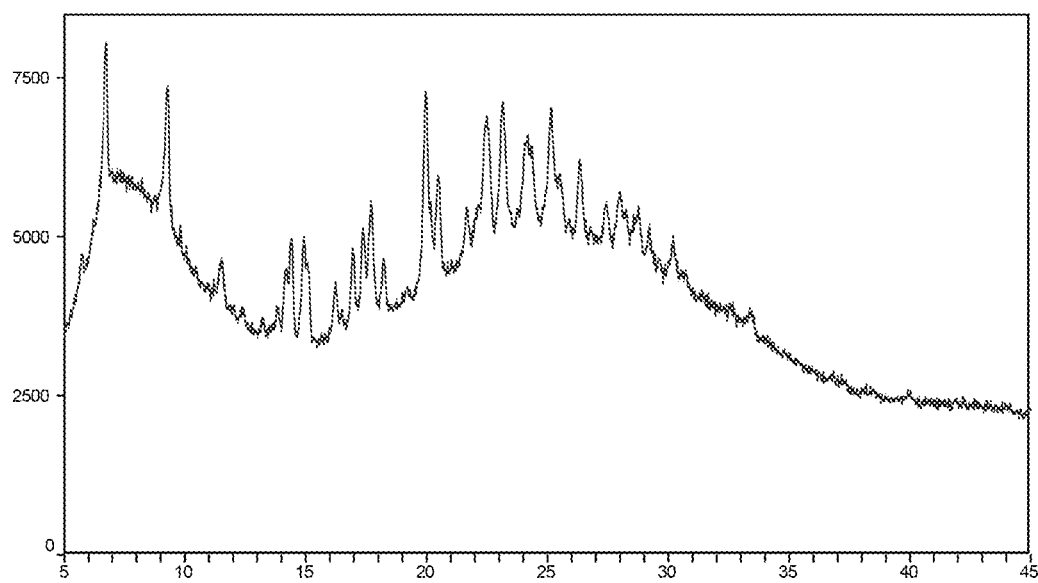
FIG. 8 is the X-ray powder diffraction spectrum of crystal form IV of a sulfate salt of the compound of formula I.

Example 8: Preparation of Crystal Form IV of a Sulfate Salt of the Compound of Formula I About 20 mg of the free base solid of the compound of formula I (amorphous) were weighed and placed in a 1.5 mL vial, and then 200 μL of ethanol as a positive solvent were added to dissolve the solid. Under stirring conditions, an equimolar amount of sulfuric acid was added to the vial at room temperature. After stirring was continued for 24 hours, a solid-liquid separation was carried out to obtain crystal form IV of the sulfate salt of the compound of formula I. The X-ray powder diffraction spectrum is shown in FIG. 8.

Figure 9:
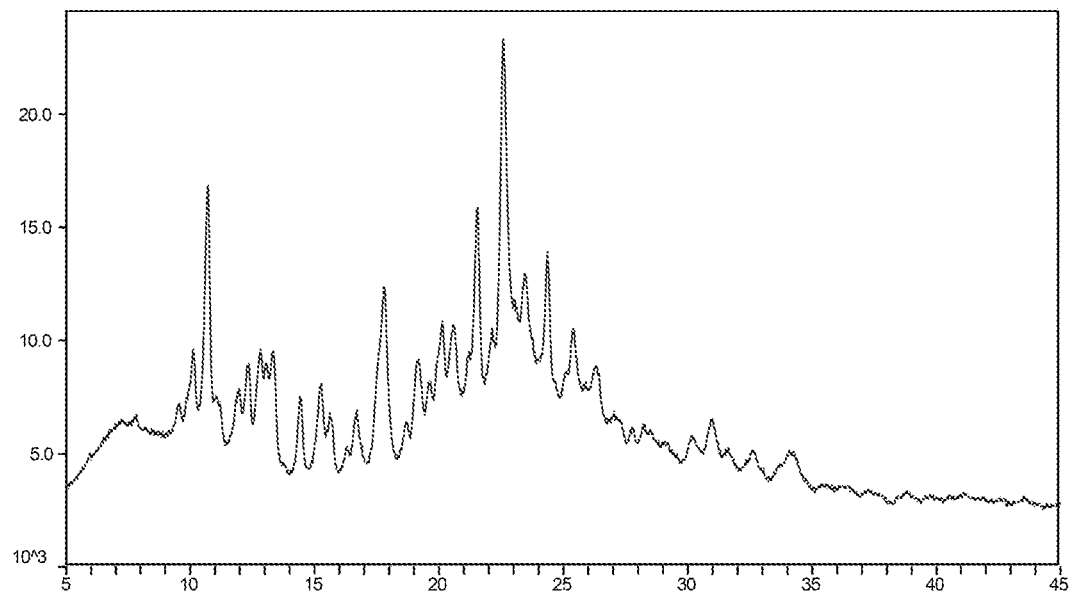
FIG. 9 is the X-ray powder diffraction spectrum of crystal form I of a phosphate salt of the compound of formula I.

Example 9: Preparation of Crystal Form I of a Phosphate Salt of the Compound of Formula I About 20 mg of the free base solid of the compound of formula I (amorphous) were weighed and placed in a 1.5 mL vial, and then 200 μL of acetonitrile as a positive solvent were added to dissolve the solid. Under stirring conditions, an equimolar amount of phosphoric acid was added to the vial at room temperature. After stirring was continued for 24 hours, a solid-liquid separation was carried out to obtain crystal form I of the phosphoric salt of the compound of formula I. The X-ray powder diffraction spectrum is shown in FIG. 9.

Figure 10:
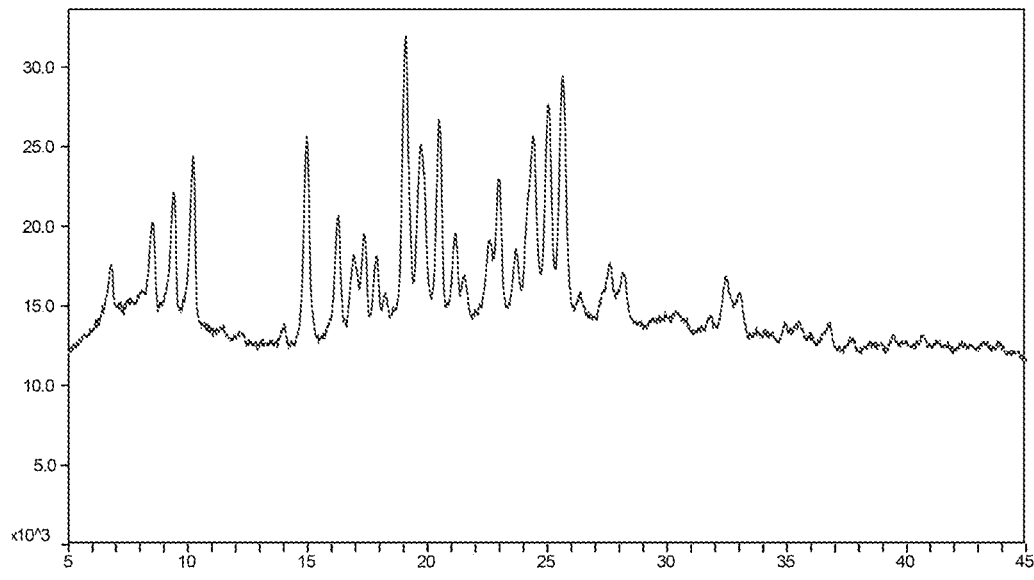
FIG. 10 is the X-ray powder diffraction spectrum of crystal form I of a mesylate salt of the compound of formula I.

Example 10: Preparation of Crystal Form I of a Mesylate Salt of the Compound of Formula I About 20 mg of the free base solid of the compound of formula I (amorphous) were weighed and placed in a 1.5 mL vial, and then 200 μL of dioxane as a positive solvent were added to dissolve the solid. Under stirring conditions, 2.5 μL of methanesulfonic acid were added to the vial at room temperature. After stirring was continued for 24 hours, a solid-liquid separation was carried out to obtain crystal form I of the mesylate salt of the compound of formula I. The X-ray powder diffraction spectrum is shown in FIG. 10.

Figure 11:
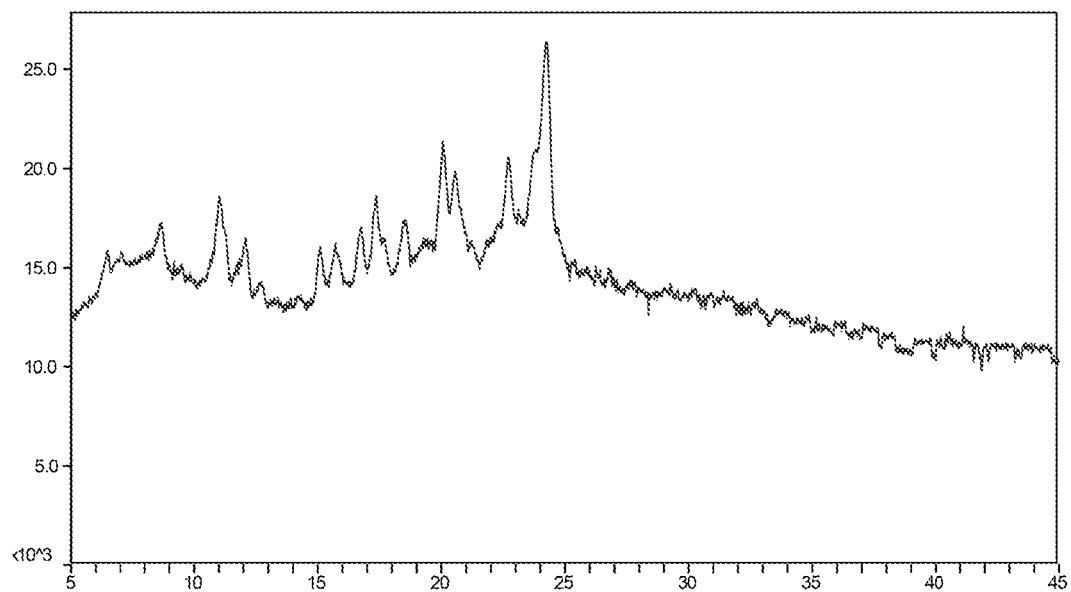
FIG. 11 is the X-ray powder diffraction spectrum of crystal form II of a mesylate salt of the compound of formula I.

Example 11: Preparation of Crystal Form II of a Mesylate Salt of the Compound of Formula I About 20 mg of the free base solid of the compound of formula I (amorphous) were weighed and placed in a 1.5 mL vial, and then 200 μL of isopropanol as a positive solvent were added to dissolve the solid. Under stirring conditions, 2.5 μL of methanesulfonic acid were added to the vial at room temperature. After stirring was continued for 24 hours, a solid-liquid separation was carried out to obtain crystal form II of the mesylate salt of the compound of formula I. The X-ray powder diffraction spectrum is shown in FIG. 11.

Figure 12:
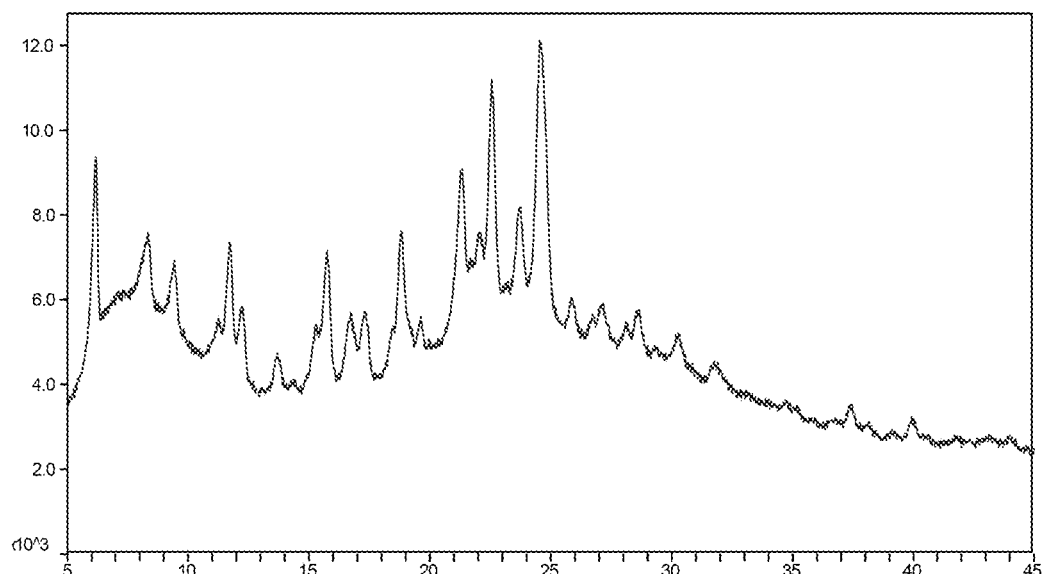
FIG. 12 is the X-ray powder diffraction spectrum of crystal form III of a mesylate salt of the compound of formula I.

Example 12: Preparation of Crystal Form III of a Mesylate Salt of the Compound of Formula I About 20 mg of the free base solid of the compound of formula I (amorphous) were weighed and placed in a 1.5 mL vial, and then 200 μL of dichloromethane as a positive solvent were added to dissolve the solid. Under stirring condition, 2.5 μL of methanesulfonic acid were added to the vial at room temperature. After stirring was continued for 24 hours, a solid-liquid separation was carried out to obtain crystal form III of the mesylate salt of the compound of formula I. The X-ray powder diffraction spectrum is shown in FIG. 12.

Figure 13:
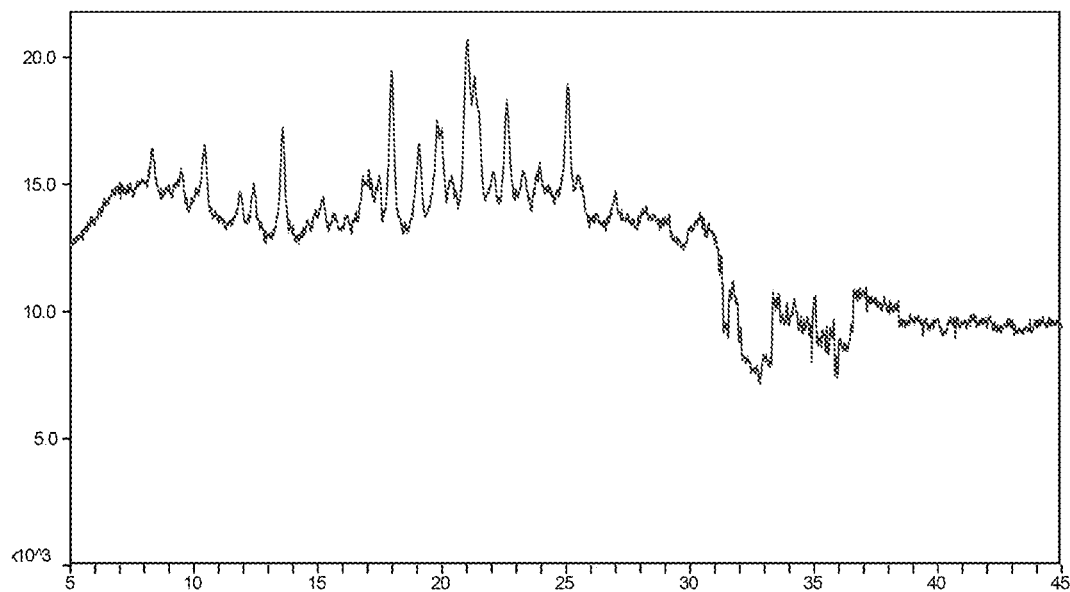
FIG. 13 is the X-ray powder diffraction spectrum of crystal form IV of a mesylate salt of the compound of formula I.

Example 13: Preparation of Crystal Form IV of a Mesylate Salt of the Compound of Formula I About 20 mg of a mesylate salt solid of the compound of formula I were weighed and placed in a 1.5 mL vial, and then 0.5 mL of methyl tert-butyl ether was added. After stirring was continued for 24 hours, a solid-liquid separation was carried out to obtain crystal form IV of the mesylate salt of the compound of formula I. The X-ray powder diffraction spectrum is shown in FIG. 13.

Figure 14:
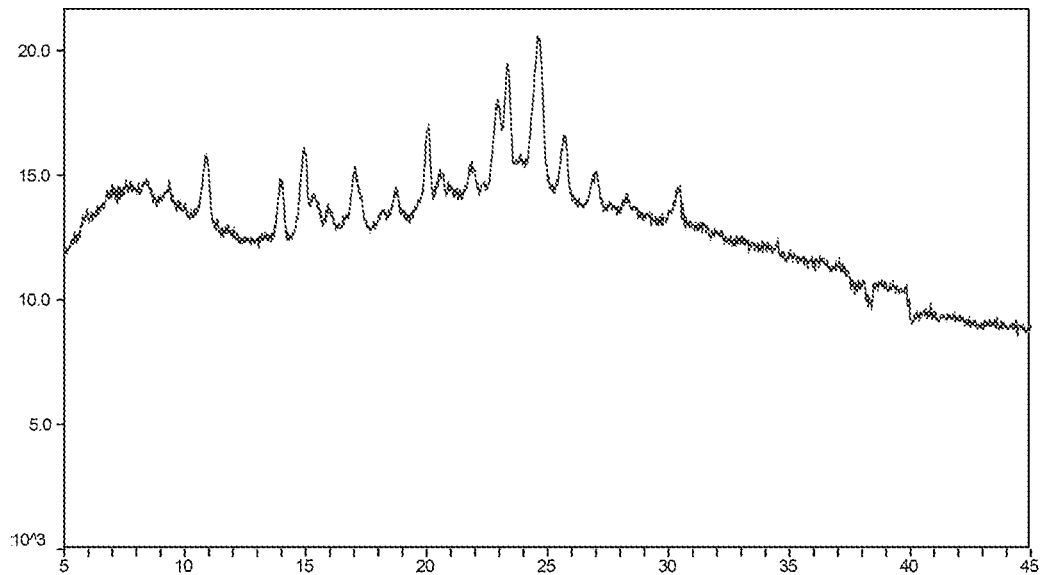
FIG. 14 is the X-ray powder diffraction spectrum of crystal form V of a mesylate salt of the compound of formula I.

Example 14: Preparation of Crystal Form V of a Mesylate Salt of the Compound of Formula I About 20 mg of a mesylate salt solid of the compound of formula I was weighed and placed in a 1.5 mL vial, and then 0.5 mL of tetrahydrofuran was added. After stirring was continued for 24 hours, a solid-liquid separation was carried out to obtain crystal form V of the mesylate salt of the compound of formula I. The X-ray powder diffraction spectrum is shown in FIG. 14.

Figure 15:
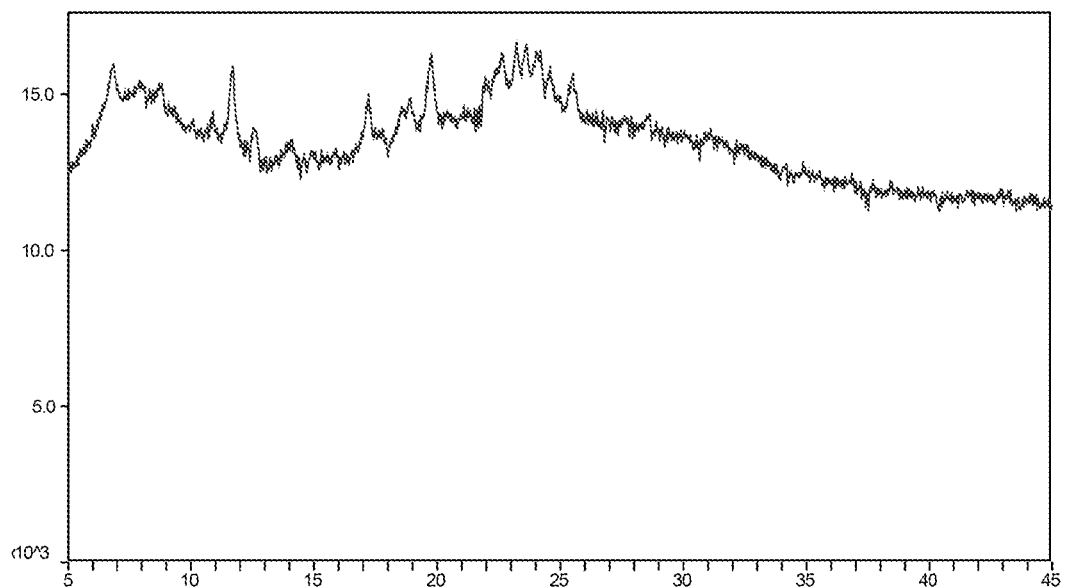
FIG. 15 is the X-ray powder diffraction spectrum of crystal form VI of a mesylate salt of the compound of formula I.

Example 15: Preparation of Crystal Form VI of a Mesylate Salt of the Compound of Formula I About 20 mg of a mesylate salt solid of the compound of formula I were weighed and placed in a 1.5 mL vial, and then 0.5 mL of isopropanol was added. After stirring was continued for 24 hours, a solid-liquid separation was carried out to obtain crystal form VI of the mesylate salt of the compound of formula I. The X-ray powder diffraction spectrum is shown in FIG. 15.

Figure 16:
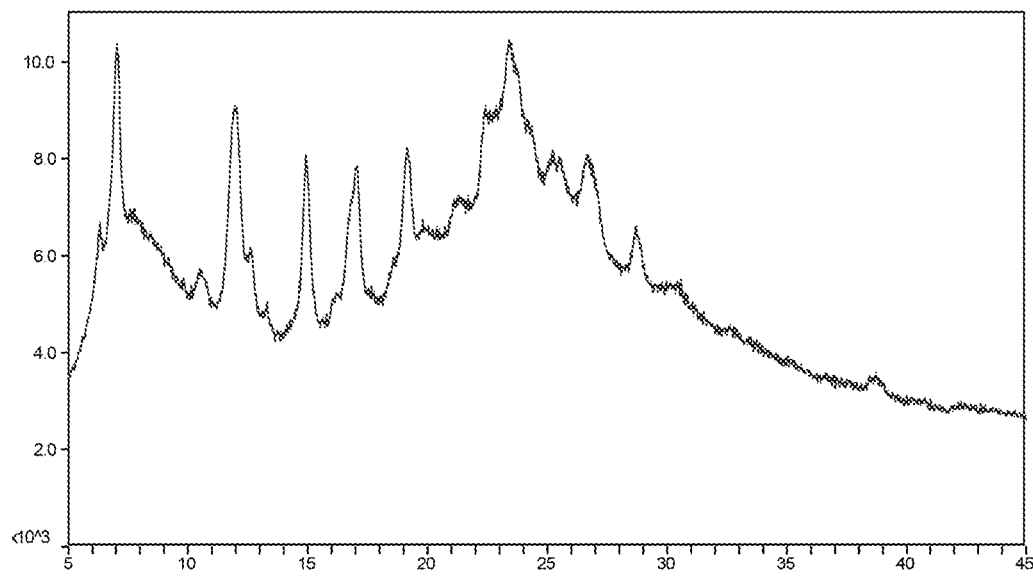
FIG. 16 is the X-ray powder diffraction spectrum of crystal form I of a fumarate salt of the compound of formula I.

Example 16: Preparation of Crystal Form I of a Fumarate Salt of the Compound of Formula I About 20 mg of the free base solid of the compound of formula I (amorphous) were weighed and placed in a 1.5 mL vial, and then 200 μL of acetonitrile as a positive solvent were added to dissolve the solid. Under stirring conditions, an equimolar amount of fumaric acid was added to the vial at room temperature. After stirring was continued for 24 hours, a solid-liquid separation was carried out to obtain crystal form I of the fumaric salt of the compound of formula I. The X-ray powder diffraction spectrum is shown in FIG. 16.

Figure 17:
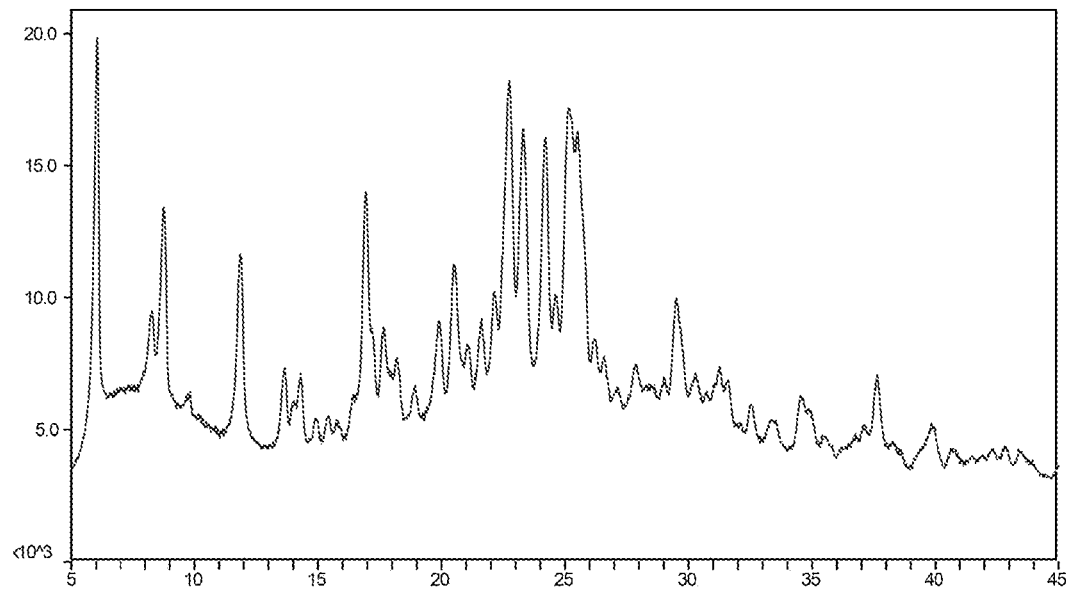
FIG. 17 is the X-ray powder diffraction spectrum of crystal form II of a fumarate salt of the compound of formula I.

Example 17: Preparation of Crystal Form II of a Fumarate Salt of the Compound of Formula I About 20 mg of the free base solid of the compound of formula I (amorphous) were weighed and placed in a 1.5 mL vial, and then 200 μL of acetone as a positive solvent were added to dissolve the solid. Under stirring conditions, an equimolar amount of fumaric acid was added to the vial at room temperature. After stirring was continued for 24 hours, a solid-liquid separation was carried out to obtain crystal form II of the fumaric salt of the compound of formula I. The X-ray powder diffraction spectrum is shown in FIG. 17.

Figure 18:
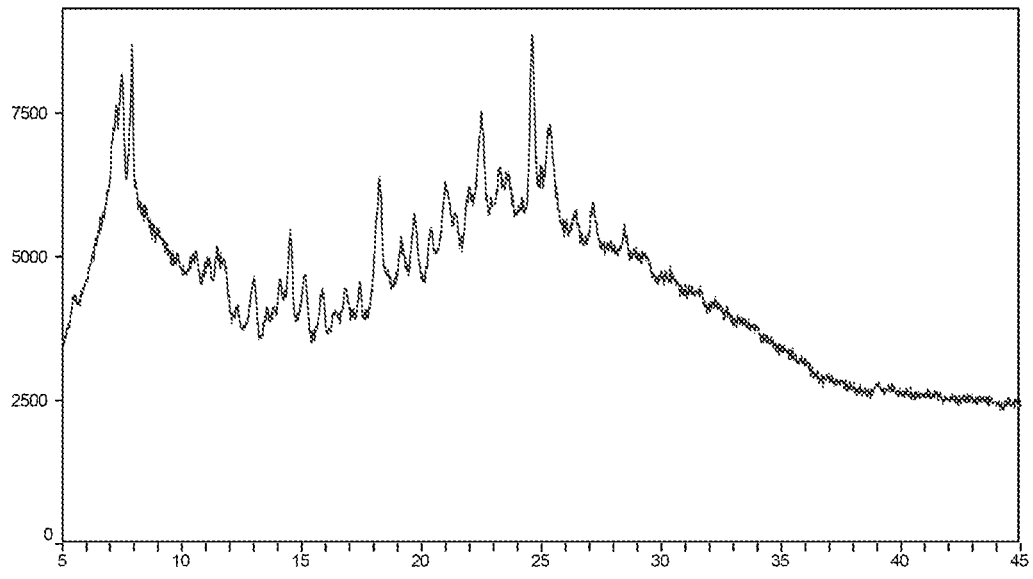
FIG. 18 is the X-ray powder diffraction spectrum of crystal form I of a maleate salt of the compound of formula I.

Example 18: Preparation of Crystal Form I of a Maleate Salt of the Compound of Formula I About 20 mg of the free base solid of the compound of formula I (amorphous) were weighed and placed in a 1.5 mL vial, and then 200 μL of acetonitrile as a positive solvent were added to dissolve the solid. Under stirring conditions, an equimolar amount of maleate acid was added to the vial at room temperature. After stirring was continued for 24 hours, a solid-liquid separation was carried out to obtain crystal form I of the maleate salt of the compound of formula I. The X-ray powder diffraction spectrum is shown in FIG. 18.

Figure 19:
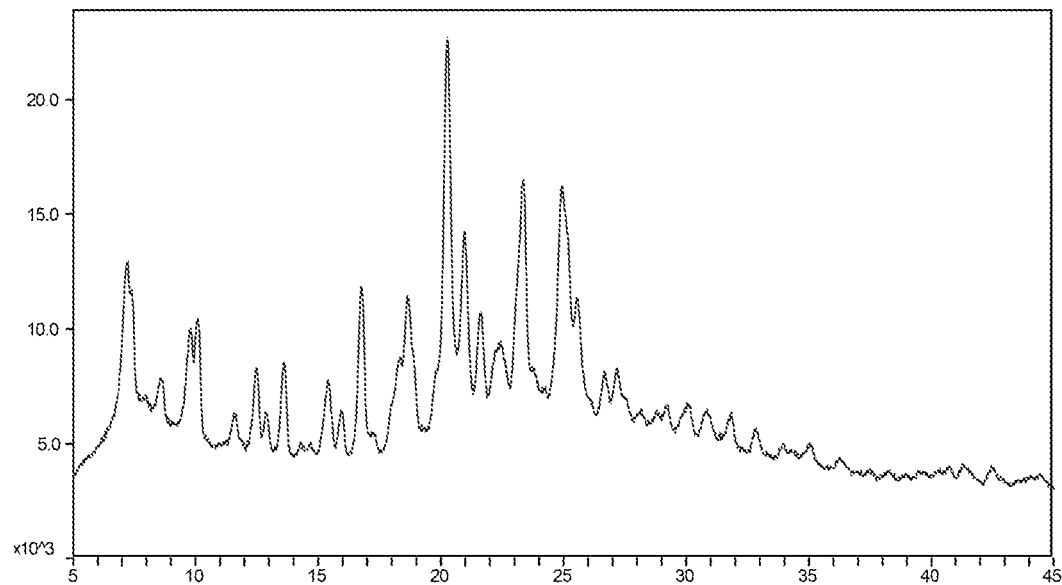
FIG. 19 is the X-ray powder diffraction spectrum of crystal form II of a maleate salt of the compound of formula I.

Example 19: Preparation of Crystal Form II of a Maleate Salt of the Compound of Formula I About 20 mg of the free base solid of the compound of formula I (amorphous) were weighed and placed in a 1.5 mL vial, and then 200 μL of ethyl acetate as a positive solvent were added to dissolve the solid. Under stirring conditions, an equimolar amount of maleate acid was added to the vial at room temperature. After stirring was continued for 24 hours, a solid-liquid separation was carried out to obtain crystal form II of the maleate salt of the compound of formula I. The X-ray powder diffraction spectrum is shown in FIG. 19.

Figure 20:
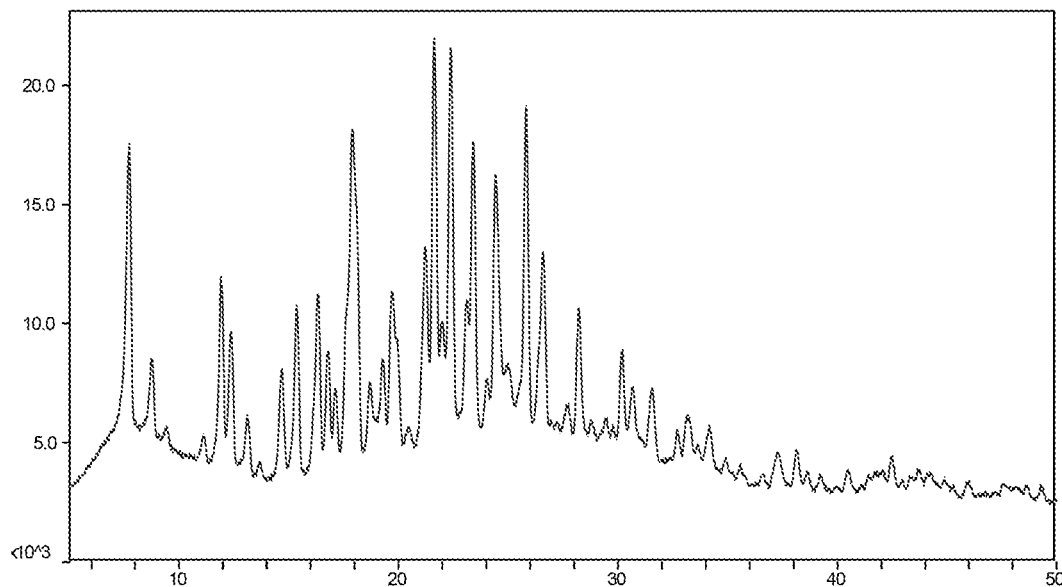
FIG. 20 is the X-ray powder diffraction spectrum of crystal form III of a maleate salt of the compound of formula I.

Example 20: Preparation of Crystal Form III of a Maleate Salt of the Compound of Formula I About 400 mg of the free base solid of the compound of formula I (amorphous) were weighed and placed in a 20 mL vial, and then 4 mL of ethyl acetate as a positive solvent were added to dissolve the solid. Under stirring conditions, an equimolar amount of maleate acid was added to the vial at room temperature. After stirring was continued for 24 hours, a solid-liquid separation was carried out to obtain crystal form III of the maleate salt of the compound of formula I. The X-ray powder diffraction spectrum is shown in FIG. 20.

Figure 21:
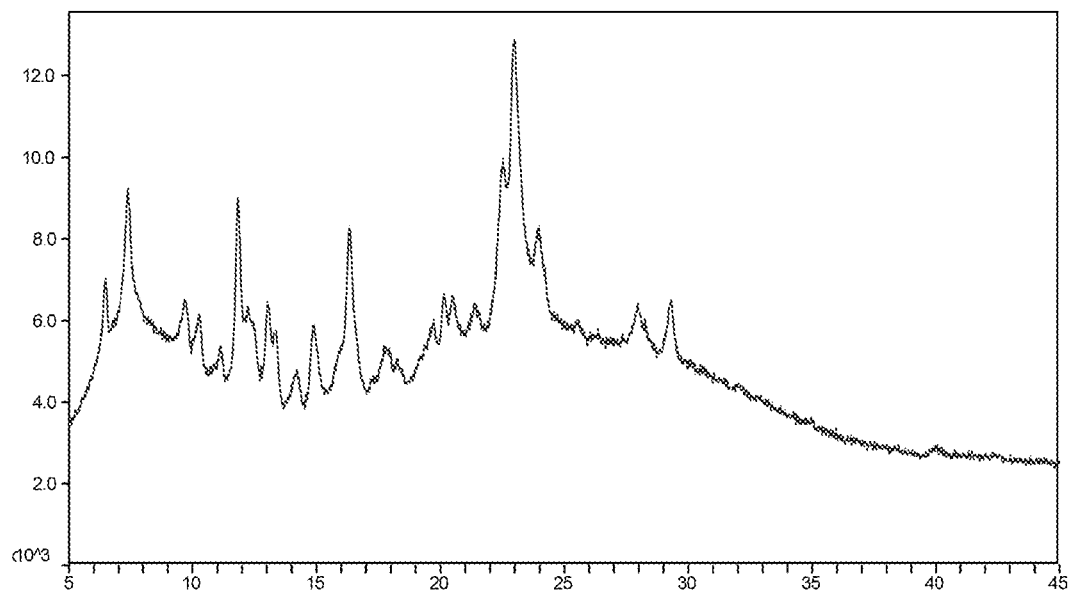
FIG. 21 is the X-ray powder diffraction spectrum of crystal form I of an acetate salt of the compound of formula I.

Example 21: Preparation of Crystal Form I of an Acetate Salt of the Compound of Formula I About 20 mg of the free base solid of the compound of formula I (amorphous) were weighed and placed in a 1.5 mL vial, and then 200 μL of acetonitrile as a positive solvent were added to dissolve the solid. Under stirring conditions, an equimolar amount of acetic acid acid was added to the vial at room temperature. After stirring was continued for 24 hours, a solid-liquid separation was carried out to obtain crystal form I of the acetic acid salt of the compound of formula I. The X-ray powder diffraction spectrum is shown in FIG. 21.

Figure 22:
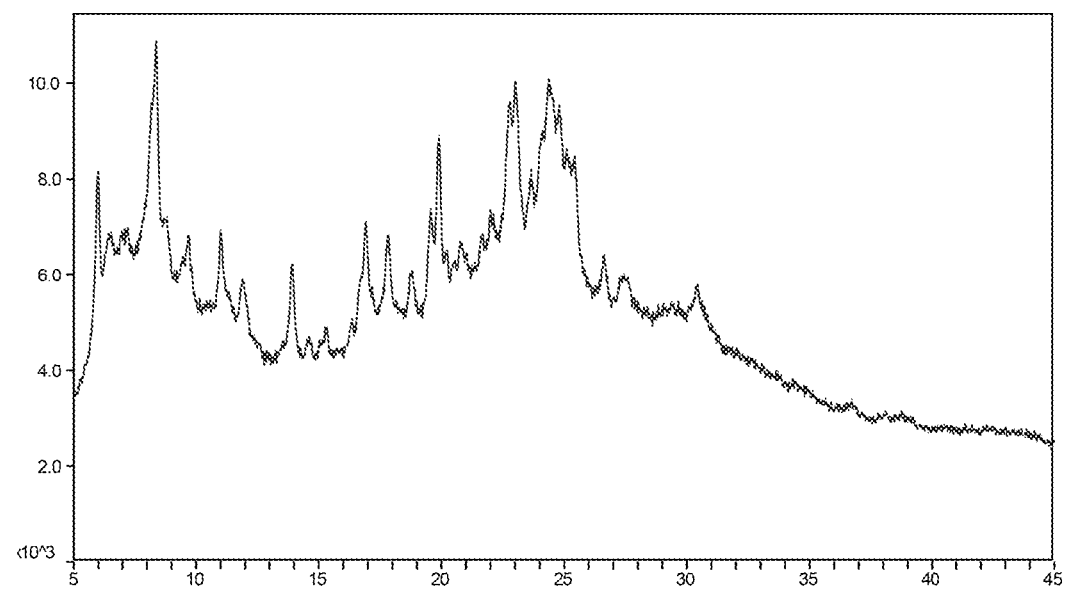
FIG. 22 is the X-ray powder diffraction spectrum of crystal form II of an acetate salt of the compound of formula I.

Example 22: Preparation of Crystal Form II of an Acetate Salt of the Compound of Formula I About 20 mg of the free base solid of the compound of formula I (amorphous) were weighed and placed in a 1.5 mL vial, and then 200 μL of ethyl acetate as a positive solvent were added to dissolve the solid. Under stirring conditions, an equimolar amount of acetic acid acid was added to the vial at room temperature. After stirring was continued for 24 hours, a solid-liquid separation was carried out to obtain crystal form II of the acetic acid salt of the compound of formula I. The X-ray powder diffraction spectrum is shown in FIG. 22.

Finally, it should be noted that the above examples are used only to illustrate the technical solution of the present invention, but are not limited to the scope of the present invention. Although the present invention has been described in detail with reference to the preferred examples, those skilled in the art would understand that the technical solution of the present invention can be modified or equivalently varied without departing from the spirit and scope of the invention, and such modifications and variations should be included in the claims of the present invention.

What is claimed is:

1. An acid salt of N-(5-((4-(1-cyclopropyl-1H-indol-3-yl) pyrimidin-2-yl)amino)-2-((2-(dimethylamino)ethyl) (methyl)amino)-4-methoxyphenyl)acrylamide (a compound of formula I), wherein the acid salt comprises an inorganic acid salt or an organic acid salt; wherein the inorganic acid salt is selected from the group consisting of hydrochloride, sulfate, hydrobromide, hydrofluoride, hydroiodide and phosphate; wherein the organic acid salt is selected from the group consisting of acetate, propionate, hexanoate, caprylate, fumarate, maleate, malonate, succinate, glutarate, adipate, sebacate, dichloroacetate, trichloroacetate, acetohydroxamate, salicylate, 4-aminosalicylate, benzoate, 4-acetylaminobenzoate, 4-aminobenzoate, caprate, cinnamate, citrate, aspartate, camphorate, gluconate, glucuronate, glutamate, erythorbate, lactate, aspartate, malate, mandelate, pyroglutamate, tartrate, lauryl sulfate, dibenzoyltartrate, 2,5-dihydroxybenzoate, 1-hydroxy-2-naphthoate, mesylate, ethyl-1,2-disulfonate, ethanesulfonate, benzenesulfonate, 4-chlorobenzenesulfonate, p-toluenesulfonate, cyclohexylsulfamate, camphorsulfonate, 1,5-naphthalenedisulfonate, naphthalene-2-sulfonate, formate, galactonate, gentisate, 2-ketoglutarate, glycolate, hippurate, isethionate, lactobionate, ascorbate, aspartate, laurate, camphorate, nicotinate, oleate, orotate, oxalate, palmitate, pamoate, stearate, thiocyanate, undecylenate, trifluoroacetate and succinate.

2. The acid salt of the compound of formula I according to claim 1, wherein the acid salt is a fumarate salt, selected from the group consisting of crystal form I of the fumarate salt and crystal form II of the fumarate salt, wherein an X-ray powder diffraction spectrum of the crystal form I of the fumarate salt comprises peaks at diffraction angles (2θ) of 7.1±0.2°, 12.0±0.2°, 14.9±0.2° and 17.1±0.2°; and wherein an X-ray powder diffraction spectrum of the crystal form II of the fumarate salt comprises peaks at diffraction angles (2θ) of 6.0±0.2°, 22.7±0.2°, 25.1±0.2° and 23.3±0.2°.

3. The acid salt of the compound of formula I according to claim 1, wherein the acid salt is a maleate salt, selected from the group consisting of crystal form I of the maleate salt, crystal form II of the maleate salt and crystal form III of the maleate salt; wherein an X-ray powder diffraction spectrum of the crystal form I of the maleate salt comprises peaks at diffraction angles (2θ) of 7.9±0.2°, 24.6±0.2°, 7.5±0.2° and 18.2±0.2°; wherein an X-ray powder diffraction spectrum of the crystal form II of the maleate salt comprises peaks at diffraction angles (2θ) of 20.3±0.2°, 24.9±0.2°, 23.4±0.2° and 16.8±0.2°; and wherein an X-ray powder diffraction spectrum of the crystal form III of the maleate salt comprises peaks at diffraction angles (2θ) of 21.6±0.2°, 22.4±0.2°, 17.9±0.2° and 25.8±0.2°.

4. The acid salt of the compound of formula I according to claim 1, wherein the acid salt is an acetate salt selected from the group consisting of crystal form I of the acetate salt and crystal form II of the acetate salt; wherein an X-ray powder diffraction spectrum of the crystal form I of the acetate salt comprises peaks at diffraction angles (2θ) of 23.0±0.2°, 11.8±0.2°, 16.3±0.2° and 7.4±0.2°; and wherein an X-ray powder diffraction spectrum of the crystal form II of the acetate salt comprises peaks at diffraction angles (2θ) of 8.4±0.2°, 19.9±0.2°, 23.0±0.2° and 24.8±0.2°.

5. A method for preparing the acid salt of the compound of formula I according to claim 1, comprises the following step of:
preparing the acid salt of the compound of formula I as follows: dissolving or dispersing the free base of the compound in an aqueous solvent or a suitable organic solvent, and then adding a liquid or solid or solution of inorganic acid or organic acid to the above system to prepare the acid salt of the compound of formula I; or, adding the free base solid to an acid solution to prepare the acid salt of the compound of formula I.

6. The method for preparing the acid salt of the compound of formula I according to claim 5, wherein the organic solvent is selected from the group consisting of methanol, ethanol, isopropanol, acetonitrile, acetone, ethyl acetate, isopropyl acetate, toluene, n-butanol, cyclohexane, dichloromethane, dimethylformamide, dimethylacetamide, dimethyl sulfoxide, dioxane, ethyl ether, n-heptane, n-hexane, methyl ethyl ketone, isooctane, pentane, dipropanol, tetrahydrofuran, dimethyl tetrahydrofuran, trichloroethane, and dimethylbenzene, or a mixture thereof.

7. A pharmaceutical composition comprising a therapeutically effective amount of the acid salt of the compound of formula I according to claim 1 and a pharmaceutically acceptable carrier.

8. The acid salt of the compound of formula I according to claim 1, wherein the acid salt is selected from the group consisting of mesylate, fumarate, maleate, and acetate.

9. The acid salt of the compound of formula I according to claim 1, wherein the acid salt is mesylate.

10. The acid salt of the compound of formula I according to claim 1, wherein the acid salt of the compound of formula I is crystal form.

* * * * *